United States Patent [19]

Terao et al.

[11] 4,393,075
[45] Jul. 12, 1983

[54] QUINONE COMPOUNDS AND THEIR USE IN SUPPRESSING THE PRODUCTION OF SRS-A IN MAMMALS

[75] Inventors: Shinji Terao, Toyonaka; Mitsuru Shiraishi, Suita; Yoshitaka Maki, Kyoto, all of Japan

[73] Assignee: Takeda Chemical Industries, Ltd., Osaka, Japan

[21] Appl. No.: 248,042

[22] Filed: Mar. 26, 1981

[30] Foreign Application Priority Data

Apr. 14, 1980 [JP] Japan .................. 55-49433
Apr. 30, 1980 [JP] Japan .................. 55-58464
Dec. 27, 1980 [JP] Japan .................. 55-186622

[51] Int. Cl.³ .................. A61K 31/12; A61K 31/275; C07C 50/00
[52] U.S. Cl. .................. 424/304; 260/396 R; 260/465 F; 424/308; 424/311; 424/317; 424/318; 424/320; 424/324; 424/331; 424/250; 560/106; 560/107; 560/255; 560/231; 562/466; 562/508; 564/180; 564/123; 568/811; 568/823
[58] Field of Search .................. 260/396 R; 424/331, 424/304

[56] References Cited

U.S. PATENT DOCUMENTS 3,728,362 4/1973 Morimoto et al. ............. 260/396 R
4,139,545 2/1979 Morimoto et al. ............. 260/396 R

FOREIGN PATENT DOCUMENTS 53-20432 2/1978 Japan .

Primary Examiner—Leonard Schenkman
Attorney, Agent, or Firm—Wenderoth, Lind & Ponack

[57] ABSTRACT

New quinone compounds of the formula:

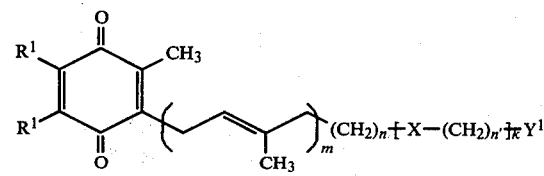

wherein $R^1$ is methyl or methoxy, or the two $R^1$ groups jointly represent —CH=CH—CH=CH—; X is —CH=CH— or —C≡C—; $Y^1$ is hydrogen, hydroxyl, carboxyl, cyano, acyloxy or —COZ in which Z is amino which may be substituted; m is zero or an integer of 1 to 3; n is zero or an integer of 1 to 10; n' is an integer of 1 to 5; k is an integer of 1 to 3; and when k is 2 or 3, n' is optionally variable within the range of 1 to 5 in each occurrence of the —X—$(CH_2)_{n'}$— group; and their hydroquinone forms and salts, have useful physiological activities such as antiasthmatic, antiallergic and blood-pressure decreasing activities.

14 Claims, No Drawings

QUINONE COMPOUNDS AND THEIR USE IN SUPPRESSING THE PRODUCTION OF SRS-A IN MAMMALS

The present invention relates to novel quinone compounds which are of value as drugs or intermediates for them.

More particularly, the compounds of the present invention are quinone compounds of the formula:

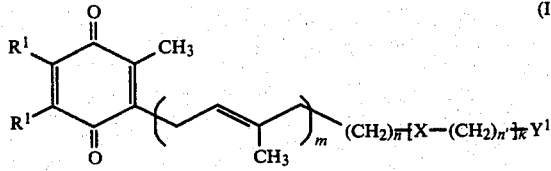

(Ia)

wherein $R^1$ is methyl or methoxy, or the two $R^1$ groups jointly represent —CH═CH—CH═CH—; X is —CH═CH— or —C≡C—; $Y^1$ is hydrogen, hydroxyl, carboxyl, cyano, acyloxy or —COZ in which Z is amino which may be substituted; m is zero or an integer of 1 to 3; n is zero or an integer of 1 to 10; n' is an integer of 1 to 5; k is an integer of 1 to 3; and when k is 2 or 3, each occurence of the n' is optionally variable within the range of 1 to 5 in —X—(CH$_2$)$_{n'}$ group and their hydroquinone forms, and pharmaceutically acceptable salts thereof.

The hydroquinone forms of the above quinone compounds (Ia) are represented by the formula:

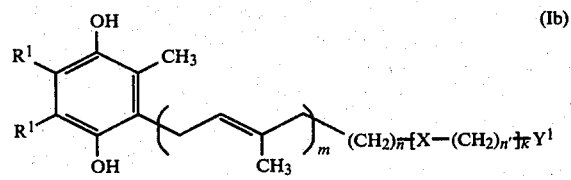

(Ib)

wherein all the symbols are as defined above.

With regard to the above-mentioned formulas (Ia) and (Ib), as examples of the substituted amino group represented by Z in —COZ, there may be mentioned mono- or di-$C_{1-4}$ alkylamino (e.g. methylamino, ethylamino, propylamino, isopropylamino, dimethylamino, diethylamino) and 5- or 6-membered cyclic amino (e.g. pyrrolidinyl, piperidino, piperazinyl). Said piperazinyl group may have a substituent such as $C_{1-4}$ alkyl (e.g. methyl, ethyl) or $C_{7-10}$ aralkyl (e.g. benzyl, 3,4,5-trimethoxybenzyl) on the nitrogen atom at its 4-position. A preferred embodiment as Z is amino, mono- or di-$C_{1-4}$ alkylamino, pyrrolidinyl, piperidino or piperazinyl, said piperazinyl being unsubstituted or substituted at the N atom of its 4-position by $C_{1-4}$ alkyl, benzyl or 3,4,5-trimethoxybenzyl.

Examples of the acyloxy group represented by $Y^1$ include $C_{2-4}$ alkanoyloxy (e.g. acetyloxy, propionyloxy), benzoyloxy, etc.

The compounds (Ia) and (Ib) of the present invention can be produced by subjecting a compound of the formula:

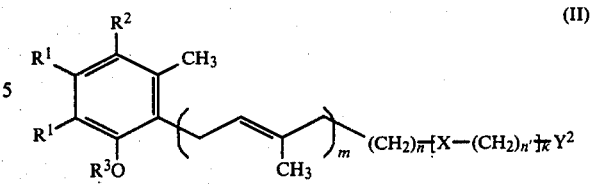

(II)

wherein $R^1$, X, m, n, n' and k are as defined above; $R^2$ is hydrogen, methoxy, methoxymethyloxy, 2-tetrahydropyranyloxy or 2-tetrahydrofuryloxy; $R^3$ is methyl, methoxymethyl, 2-tetrahydropyranyl or 2-tetrahydrofuryl; $Y^2$ has the same meaning as $Y^1$ defined above, or is 2-tetrahydropyranyloxy or 2-tetrahydrofuryloxy, to a reaction for removal of the protective group, and then, if necessary, subjecting the deprotected compound to oxidation.

With regard to the above-mentioned formula (II), the 2-tetrahydropyranyloxy and 2-tetrahydrofuryloxy groups in $Y^2$ are converted into the hydroxyl groups through the protective group removal reaction, while other groups correspond to those in $Y^1$, respectively.

As the protective group removal reaction for the compound (II), there may be mentioned, by way of example, hydrolysis, oxidation for removal of the protective group, etc. Such hydrolysis is normally conducted in an aqueous organic solvent (e.g. acetone, acetonitrile, tetrahydrofuran, 1,2-dimethoxyethane, ethanol, methanol) in the presence of an acid catalyst (e.g. sulfuric acid, camphorsulfonic acid, p-toluenesulfonic acid). The reaction temperature varies depending on the type of the protective groups to be removed and, normally, the reaction is conducted at a temperature within the range of 0° C. to 70° C. The protective groups, which can be easily removed by the hydrolysis reaction, include methoxymethyl, 2-tetrahydropyranyl, 2-tetrahydrofuryl and others. As the compound to be obtained by the hydrolysis, there may be mentioned the above hydroquinone forms (Ib) or phenol compounds of the formula:

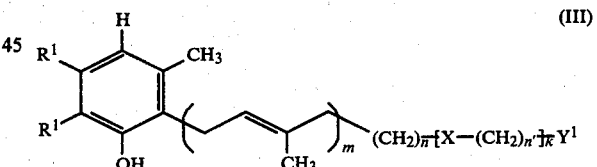

(III)

wherein each of the symbols is as defined above. The compounds (III) possess pharmacological activities similar to those of the compounds (Ia) and (Ib).

The oxidation reaction for removal of the protective group of the compound (II) is conducted by using, for example, a divalent silver compound (e.g. AgO) or cerium compound [e.g. Ce(NH$_4$)$_2$(NO$_3$)$_6$]. Thus, the compound (II) in water or an aqueous organic solvent (e.g. dioxane, acetonitrile) is reacted with the use of AgO in the presence of nitric acid or Ce(NH$_4$)$_2$(NO$_3$)$_6$ in the presence of trimellitic acid-pyridine or pyridine-2,6-dicarboxylic acid or its N-oxide, pyridine-2,4,6-tricarboxylic acid or its N-oxide, etc. The reaction temperature is normally in the range of about 0° C. to 30° C. Said oxidative protective group removal reaction is particularly suited for removal of two methoxy groups situated in the para positions, and permits simultaneously removal of the protective groups and production of the quinone compound (Ia).

The hydroquinone compounds (Ib) and phenol compounds (III), which are formed when a hydrolysis reaction is employed as the reaction for removal of the protective group, can be converted into the quinone compounds (Ia) by subjecting them further to an oxidation reaction, if necessary. Such oxidation is normally carried out in a suitable aqueous organic solvent (e.g. dimethylformamide, acetonitrile, dioxane, tetrahydrofuran, methanol, ether, 1,2-dimethoxyethane) with the use of a mild oxidizing agent (e.g. Fremy's salt [.O—N(-SO$_3$K)$_2$], ferric chloride, silver oxide, air). The reaction temperature is normally in the range of about 0° C. to 30° C.

The quinone compound (Ia) where the radical represented by $Y^1$ is a —COZ group can also be produced by subjecting to the per se known amidation reaction (e.g. the reaction with the use of dicyclohexylcarbodiimide or the active ester method utilized in the peptide synthesis) the quinone carboxylic acid compound (Ia) where $Y^1$ is a carboxyl group.

Also, the objective compound (Ia) or (Ib) of the present invention where the radical represented by X is —CH=CH— can be produced by catalytic partial reduction of the compound (Ia) or (Ib), where the radical represented by X is —C≡C—, in the presence of Lindlar catalyst. Reduction with Lindlar catalyst is conducted in a solvent such as methanol, ethanol and ethyl acetate after adding quinoline in an amount of about 1/10 to 2 times that of the catalyst to adjust the catalytic activity. The double bond resulting from said partial reduction is mainly a cis-olefin bond

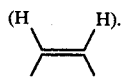

The quinone compounds (Ia) and their hydroquinone forms (Ib) thus produced can be isolated and collected by separation and purification procedures per se known (e.g. chromatography, distillation, crystallization) and others.

Furthermore, the quinone compounds (Ia) and hydroquinone compounds (Ib) of the present invention should be considered as pharmacologically equivalent, because they are convertible into each other under physiological conditions. Generally, the hydroquinone compounds (Ib) are chemically susceptible to oxidation and are preferably handled as the quinone compounds (Ia). The hydroquinone compounds (Ib) can be converted into the stable form such as the above-mentioned compounds (II) by introducing the protective group into the hydroxyl group by way of a reaction known per se (e.g. etherification, benzylation, acylation).

The compounds (Ia) and (Ib) of the present invention exert profound effect upon the metabolic pathway for polyunsaturated fatty acids (PUFA) such as linoleic acid, linolenic acid, dihomo-γ-linolenic acid, arachidonic acid and eicosapentaenoic acid, particularly the metabolic pathways involving lipoxygenase and cyclooxygenase. For example, the compounds suppress production of SRS-A (slow reacting substance of anaphylaxis), the substance known to cause immediate allergy, and simultaneously inhibit production of 5-hydroperoxyeicosatetraenoic acid (5-HPETE) and 5-hydroxyeicosatetraenoic acid (5-HETE).

5-HPETE is one of hydroperoxy-fatty acids produced from arachidonic acid by lipoxygenase in human polymorphonuclear leukocytes, rat mastocytes, etc. and an important intermediate for SRS-A, as well [Proc. Natl. Acad. Sci., vol. 76, pp. 4275 (1979)]. The objective compounds (Ia) or (Ib) of the present invention, by suppressing production of 12-hydroperoxyeicosatetraenoic acid (12-HPETE) liberated for example from human blood platelets, leukocytes and mastocytes, and rat peritoneal cells, and by simultaneously inhibiting liberation of various hydroperoxy-fatty acids produced from PUFA, get involved in the defense in living tissues and cells against hydroperoxy-fatty acids, and are useful for improvement of the prostaglandin-thromboxane metabolism. For example, they are of use in preventing the prostaglandin-I$_2$ (PGI$_2$) synthatase from being inactivated by hydroperoxy-fatty acids. In addition, the compounds (Ia) and (Ib) of the present invention inhibit autoxidation of arachidonic acid in the concentration of near 1 μM.

Based on their improvement of the metabolism of PUFA, particularly their inhibitory action on production of hydroperoxy-fatty acids, namely anti-oxidizing activity, the compounds (Ia) and (Ib) of the present invention exhibit in mammals various physiological actions such as antiasthmatic, antiallergic, blood-pressure decreasing, arteriosclerosis-improving, atherosclerosis-improving, platelet-aggregation improving, renal-, cerebral- and coronary-circulation improving, anti-digestive-tract-ulcer, diuretic, immuno-regulatory and bacterial-infection defending actions. Thus, they are of value as drugs, such as an antiasthmatic agent, antiallergic agent, antihypertensive agent, antiulcer agent, diuretic agent, antithrombotic agent, cerebral-circulation improving agent, coronary artery improving agent, immuno-regulating agent, bacterial-infection defense promoting agent and prostaglandin-thromboxane metabolism improving agent, in the treatment or prophylaxis of, bronchial asthma, allergosis, hypertension, peptic ulcer, cerebral thrombosis, ischemic myocardial infarction, coronary artery disorders, atherosclerosis, immuno-deficiency, disorder of regulation in prostaglandin- and thromboxane-biosynthesis, etc. In particular, the present compounds are useful as antiasthmatic, antiallergic, antiulcer and cerebral-circulation improving agents.

The compounds of the present invention are low in toxicity and can be safely administered either orally or parenterally, as such or as a pharmaceutical composition [e.g. tablets, capsules (inclusive of soft capsules and microcapsules), solutions, injections and suppositories] formed by mixing them with pharmaceutically acceptable carriers, excipients, etc. conventional per se. The dosage varies depending upon type of hosts, administration route, symptom, etc. In the case of oral administration to patients with hypertension or bronchial asthma, they are given suitably in a single dose within the range of, normally about 0.2 mg/kg to 25 mg/kg of body weight, preferably about 0.5 to 10 mg/kg of body weight, 1 to 3 times daily.

In cases in which the compounds (Ia) and (Ib) of the present invention are employed as the above drugs, the quinone compounds (Ia) are generally preferable in terms of stability, etc. Among (Ia), the compound where $R^1$ is methyl or methoxy and X is —C≡C— is preferred in the case of the inhibitory action on the production of SRS-A, and the compound where $R^1$ is methoxy is preferable in the case of antiulcer action. In both of the above cases, preferably, $Y^1$ is hydroxyl, and m is zero or 1, while n, n' and k are integers of 1 to 4, 1 to 3 and 1 to 2, respectively.
The starting compounds (II) useful in the present invention can be produced, for example, by the following procedure:
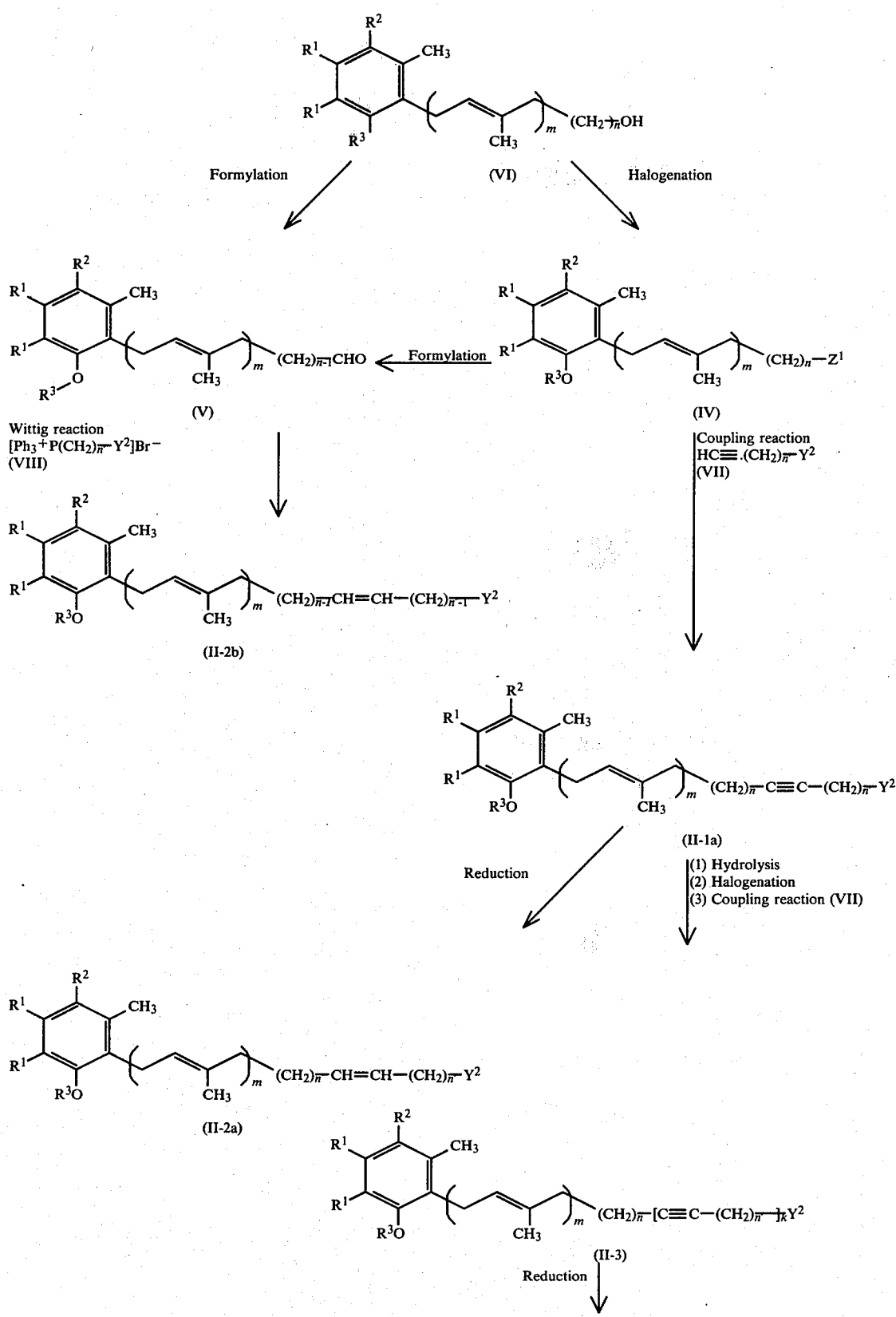

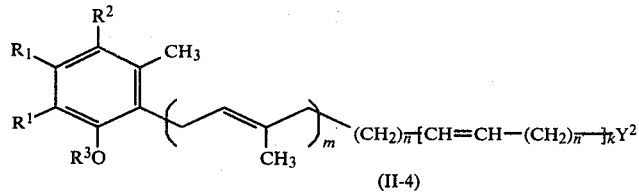

(II-4)

[wherein Ph is phenyl, $Z^1$ is halogen (e.g. Br, I) and other symbols are as defined above]

The starting compounds (VI) in the present invention may be prepared by the production methods described for example in the Japanese Unexamined Patent Publication Nos. 128932/1976 and 7737/1981 (Application No. 84291/1979), and Japanese Patent Application No. 49433/1980.

The alcohol compound (VI) can be converted to the corresponding halogen compound (IV) or aldehyde compound (V) by halogenating or formylating it. The halogen compound (IV) can be derived by treating the alcohol compound (VI) with phosphorus tribromide or treating a sulfonyl ester form of the alcohol compound (VI) with a halide.

The bromination reaction of the alcohol compound (VI) is conducted in dichloromethane, chloroform, ether, isopropyl ether or tetrahydrofuran at a temperature within the range of 0° C. to 70° C., with the use of ⅓ to 1 equivalent mole of phosphorus tribromide.

The production of the halogen compound (IV) via sulfonyl ester is carried out by way of the following reaction: the alcohol compound (VI), by the action of methanesulfonyl chloride or p-toluenesulfonyl chloride in an organic solvent (e.g. methylene chloride, chloroform, ether) in the presence of an organic base (e.g. triethylamine, pyridine), is derived into the corresponding methanesulfonyl or p-toluenesulfonyl ester, which, on treating at room temperature or under heating in a halogen compound (e.g. sodium chloride, sodium bromide, potassium bromide, sodium iodide, potassium iodide) and an organic solvent (e.g. acetone, dimethylformamide, dimethylsulfoxide), can yield the corresponding halogen compound (IV).

The aldehyde compound (V) can be derived by oxidizing the alcohol compound (VI) or halogen compound (IV). In the oxidation of the alcohol compound (VI), for example, the reaction with sulfur trioxide-pyridine complex and triethylamine in pyridine-anhydrous chromic acid or dimethylsulfoxide and the like are employed, and, in the case of the halogen compound (IV), for example, treatment with silver tetrafluoroborate (AgBF$_4$)-triethylamine in dimethylsulfoxide affords the aldehyde compound (V).

The halogen compound (IV) or aldehyde compound (V) thus obtained is converted into the compound (II-1a) or (II-2b) by subjecting it to a coupling reaction or the Wittig reaction.

The coupling reaction with the acetylene compound (VII) is conducted by the action of the halogen compound (IV) in liquid ammonia or an organic solvent (e.g. tetrahydrofuran, hexamethylphosphoramide, dimethylformamide, dimethylsulfoxide) in the presence of sodium amide or lithium amide, or in an organic solvent (e.g. diethyl ether or tetrahydrofuran) in the presence of ethyl magnesium bromide and a catalytic amount of copper ion, thereby forming the compound (II-1a).

The acetylene compound (VII), which is employed in the coupling reaction, includes, by way of example, 5-hexyne carboxylic acid, 1-hydroxypent-4-yne, 1-hydroxybut-3-yne, propargyl alcohol and their tetrahydropyranyl ethers.

The coupling reaction in liquid ammonia or an organic solvent is normally conducted under an inert gas atmosphere at a temperature of about −30° C. to −70° C., while the Grignard type coupling reaction in an organic solvent is carried out at room temperature or at the boiling point of the solvent, using a copper catalyst (e.g. cuprous cyanide, cuprous bromide, cuprous iodide). The reaction mixture is subjected to isolation and purification by per se conventional procedures (e.g. solvent extraction silica-gel chromatography) to give the compound (II-2b).

The compound (II-1a) can be derived by the reaction of the aldehyde compound (V) with the Wittig reagent (VIII). As the Wittig reagent, there may be mentioned, for example, [Ph$_3$P$^+$(CH$_2$)$_4$COOH]Br$^-$, [Ph$_3$P$^+$(CH$_2$)$_5$—COOH]Br$^-$, etc., while as the solvent, there may be mentioned benzene, toluene, ether, tetrahydrofuran, dioxane, 1,2-dimethoxyethane, dimethylsulfoxide, etc., either solely or as mixed solvents. The reaction is conducted under an inert gas atmosphere and in the presence of a basic compound (e.g. n-butyllithium, methyllithium, sodium hydride, etc.), normally at −10° C. to +40° C. After the completion of the reaction, the compound (II-2b) is obtained by separation and purification of the reaction product by a conventional procedure.

The compound (II-1a) or (II-2b) produced by the above procedure can be utilized as the starting compound (II) itself, but can also be converted into other starting compounds (II) by allowing the reaction to proceed further.

Thus, among the compounds (II-1a) obtained in the above coupling reaction step, the compound where Y$^2$ is a hydroxyl group can be subjected to the above-mentioned halogenation reaction to thereby led to the corresponding halide which can form the longer acetylene compound (II-3) by the similar coupling reaction with the above-mentioned acetylene compound (VII). If necessary, the similarly repeated coupling reaction can also afford an even longer acetylene compound (II-3). In the case of the repeated coupling reaction, n' in the acetylene compound (VII) can be changed to any integer of 1 to 5. In cases in which the compound of the formula (II-3) where k is not less than 2 and n' is 1 is produced, preferred is the coupling reaction in tetrahydrofuran or diethyl ether with the use of Grignard reagent.

The compound (II-3) thus obtained can be utilized as the starting compound (II) itself, and the compounds (II-1a) and (II-3) can be converted to the olefin compound (II-2a) or (II-4) by partial reduction of the acetylene bond.

The partial reduction is, for example, by means of catalytic reduction with the Lindlar catalyst or partial reduction with lithium aluminum hydride. The reduction with the Lindlar catalyst can be conducted under the same conditions as described above. Reduction with lithium aluminum hydride is carried out by a reaction under reflux in a solvent of ether or tetrahydrofuran under an inert gas atmosphere.

The geometrical configuration of the di-substituted double bond in the olefin compounds (II-2a) and (II-4) as obtained in the above reduction is the cis-oriented olefin bond in the case of the reduction with the Lindlar catalist, while it is the trans-oriented olefin bond in the case of the reduction with lithium aluminum hydride.

The compounds (II-1a), (II-2a), (II-2b), (II-3) and (II-4) as obtained in the above reaction are all utilizable as the starting compound (II) themselves and, if necessary, can be converted to e.g. the cyano and amide compounds (II) by way of the conventional, known reactions such as protective-group removal reaction, reaction of converting a halogen compound into a nitrile group, esterification or amidation reaction of a carboxyl compound.

The production of the starting compound (VI) by the procedure described in Japanese Patent Application No. 49433/1980 will be explained hereinafter in detail.

The application relates to a process for producing a phenol compound having a tetrahydrofur-2-yl group at its ortho position characterized in that said process comprises acting an acid catalyst under anhydrous conditions on a tetrahydrofur-2-yl ether of a compound having a phenolic hydroxyl group with at least one of the ortho positions being unsubstituted.

As the acid catalyst in the above process, there may be mentioned organic sulfonic acids such as p-toluenesulfonic acid, camphorsulfonic acid and methanesulfonic acid, trifluoroacetic acid, sulfuric acid, boron trifluoride diethyl ethereate and the like, and the amount of these to be used is in the range of about 1/100 to 1/5 equivalent, preferably about 1/30 to 1/10, against an ether compound as the starting compound.

The reaction is carried out under anhydrous conditions, whereby as the solvent for the reaction, normally, use is made of anhydrous solvents such as dichloromethane, chloroform, toluene, benzene and isopropyl ether. The reaction temperature is normally in the range of room temperature to about 70° C. The reaction is desirably carried out under an atmosphere of an inert gas, and the reaction temperature varies with types of compounds to be reacted but is normally in the period of 1 to 10 hours. The objective compound produced in the reaction solution can be easily isolated by means of conventional separation and purification procedures (e.g., silica gel chromatography, distillation under reduced pressure) after neutralization of the acid catalyst.

The above-mentioned process is applied to the tetrahydrofur-2-yl ethers of compounds having a phenolic hydroxyl group with at least one of the ortho positions being unsubstituted [in some instances, hereinafter referred to briefly as "compound (IX)"], as described above. Such compounds having a phenolic hydroxyl group, which are not limited to simple phenol and its derivatives, mean the phenols as taken in a broad sense including for example catechol, pyrogallol, resorcinol, catecholamine derivatives, 5-hydroxytryptamine (serotonin), 5-hydroxyindole, etc. The reaction for etherification of such compounds with 2,3-dihydrofuran in the presence of an acid catalyst or with 2-chlorotetrahydrofuran in the presence of a base can afford the tetrahydrofur-2-yl ether compounds (IX). As the acid catalyst may be mentioned the same acid catalysts as those mentioned above, and their sufficient amount to be used is in the range of about 1/500 to 1/100 equivalent against a starting compound. In the case of the reaction with 2,3-dihydrofuran, the reaction temperature is normally in the range of 0° to 40° C. In this case, the acid catalyst is further added after the completion of the etherification reaction, while the reaction temperature is increased, if necessary, whereby the rearrangement can be consecutively carried out. By employing the catalyst amount and reaction temperature for the rearrangement reaction from the very beginning of the etherification, furthermore, the etherification and rearrangement can be carried out in one step as well. As examples of the base being useful in the etherification with 2-chlorotetrahydrofuran, there may be mentioned triethylamine, pyridine, sodium hydride, etc. As the solvent for the reaction, use is made of dichloromethane, chloroform, dimethylformamide, dimethylacetamide, etc.

As one specific example of the above compound (IX), there may be mentioned, by way of example, ether compounds of the formula:

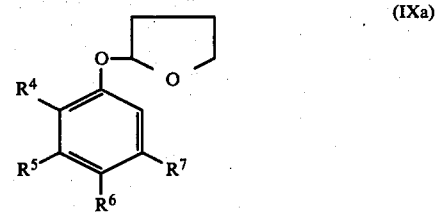

(IXa)

wherein $R^4$, $R^5$, $R^6$ and $R^7$ are independently hydrogen, hydroxyl, methyl or methoxy; any two neighboring groups of $R^4$, $R^5$, $R^6$ and $R^7$ jointly represent —CH=CH—CH=CH—.

In the above process, the tetrahydrofur-2-yl group of the compound (IX) undergoes rearrangement into the position adjacent to the phenolic hydroxyl group or the ortho position, thereby yielding the objective phenols having a tetrahydrofur-2-yl group in the said ortho position [in some instances, hereinafter referred to briefly as "compound (X)"]. Consequently, utilization of the compounds (IXa) as a starting compound, for example, affords the objective compounds of the phenols of the formula:

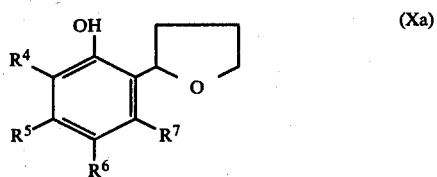

(Xa)

wherein all the symbols are as defined above.

According to the process mentioned above, the tetrahydrofur-2-yl group can be introduced into the ortho position of phenols in very high yields and selectively under mild reaction conditions.

The compounds (X) themselves, as produced by the present invention, are novel compounds, and are of value as intermediates for producing various drugs (e.g., catecholamines, naphthoquinones, benzoquinones, etc.). Thus, the tetrahydrofur-2-yl group in the ortho position of the compounds (X), by the catalytic reduction leading to ring-opening, can be easily converted into a 4-hydroxybutyl group, whereupon the resulting 4-hydroxybutyl group, when, for example, halogenated to a reactive halogenobutyl group becomes susceptible of the extension of its butyl chain, thus permitting the favorable production of varieties of valuable phenol derivatives. The ring-opening reaction by the catalytic reduction is carried out, with the use of acid catalyst (e.g., sulfuric acid, perchloric acid, etc.) and reducing catalyst (e.g., palladium, platinum, etc.), in a solvent such as acetic acid and ethyl acetate under applied pressure and warming. The halogenation is conducted, for example, by producing the corresponding sulfonyl ester with methanesulfonyl chloride or p-toluenesulfonyl chloride, followed by treating with sodium bromide or sodium iodide by a conventional procedure. In these reactions, if necessary, the phenolic hydroxyl group may be protected in advance and subjected to reaction.

By way of example, the following are the routes of the phenols (Xa) to valuable drug compounds or the compounds (VI)

The oxidation in the step A as described above is carried out with the use of a mild oxidizing agent (e.g., Fremy's salt, silver oxide, ferric chloride, etc.). The introduction of a protective group in the step B is conducted by introducing a group normally employed for protecting the phenolic hydroxyl group such as methyl, benzyl, methoxymethyl and tetrahydropyranyl groups by procedures known per se. The halogenation in the step B is carried out by the procedure described hereinbefore. The reaction of (XIIa) with (XIV) in the step C is carried out by the Wittig reaction in the case of aldehydes utilized as (XIV) and by the condensation reaction under acidic conditions in the case of acetylenes or sulfones used as (XIV), respectively. In cases in which aldehydes (XIV) are utilized, M is 1, while in the case of acetylenes, M is 2, and in the case of sulfones, M is 0. The olefin compounds or acetylene compounds obtained by these reactions can be derived into the objective quinone compounds (XIIIb) by the catalytic reduction by means of conventional procedures, followed by removal of protective group and/or by oxidation. Fur-

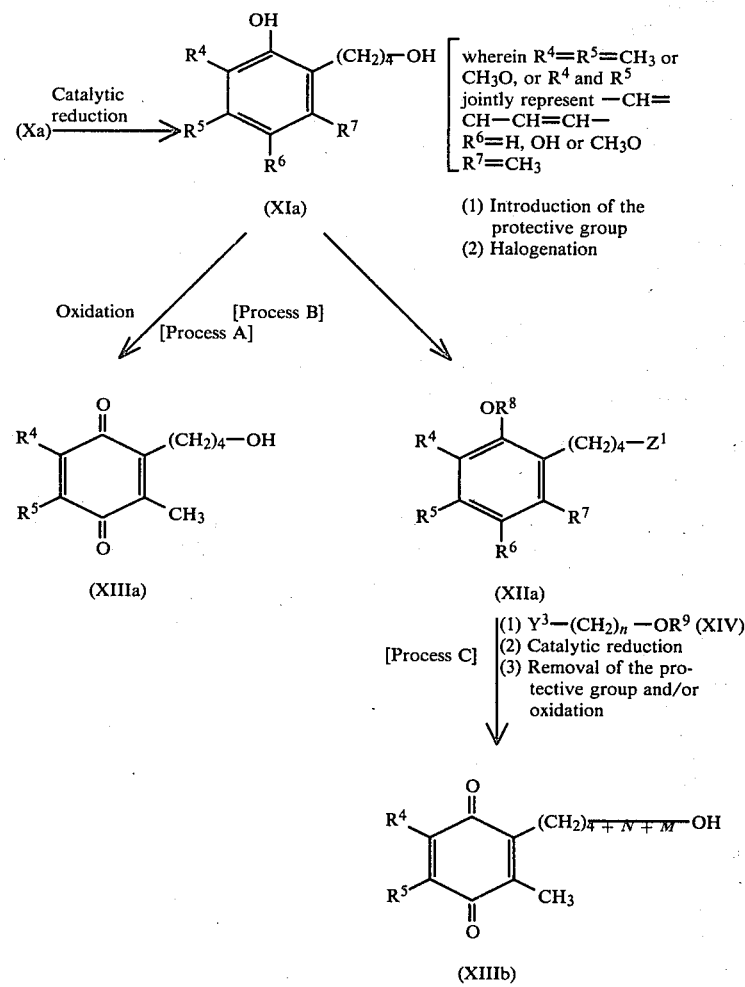

[wherein $R^8$ is a protective group for the phenolic hydroxyl group; $R^9$ is a protective group for the alcoholic hydroxyl group; $Z^1$ is halogen (e.g., Br or I), $-P^+(C_6H_5)_3I^-$ or $-P^+(C_6H_5)_3Br^-$; $Y^3$ is formyl, $CH\equiv C-$ or p-toluenesulfonyl; N is an integer of 0 to 18; M is an integer of 0 to 2, with (N+M) representing an integer of 1 to 18].

ther, the sulfone compounds can be derived into (XIIIb) by desulfonation under basic conditions followed by treatment of the resulting olefin compounds in the same manner as described above.

The above compounds (XIIIa) and (XIIIb) are, for example of value as immunostimulating agent, tissue metabolism activator (therapeutic agents for cerebral circulation disturbance, cardiac insufficiency, hypertension, etc.) and the like [refer to U.S. Pat. No. 4,139,545 (Japanese Patent Unexamined Publication No. 128932/1967), European Patent Publication No. 21841 and Japanese Patent Application No. 171125/1979].

The compounds (XIa) and (XIIa) are included in the scope of the compounds (VI) and (IV) mentioned hereinbefore and are useful as intermediates for the production of the present compounds (Ia) and (Ib).

The following examples illustrate the present invention in more detail, but they are not intended to limit its scope. The symbols in the tables shown below designate the following chemical formulas, respectively.

| Symbol | Formula | Symbol | Formula |
|---|---|---|---|
| Q | CH₃O, CH₃ / CH₃O (benzoquinone with two OCH₃, one CH₃) | Q₁ | CH₃O, CH₃ / CH₃O, OH (hydroquinone) |
| Q₂ | CH₃O, OCH₃, CH₃ / CH₃O, OCH₃ | Q₃ | CH₃O, OCH₂OCH₃, CH₃ / CH₃O, OCH₂OCH₃ |
| E | CH₃, CH₃ / CH₃, CH₃ (benzoquinone) | E₁ | CH₃, OCH₃, CH₃ / CH₃, OCH₃ |
| K | naphthoquinone with CH₃ | K₁ | naphthalene with OCH₃, CH₃, OCH₃ |

EXPERIMENTAL EXAMPLE

The inhibitory action on SRS-A production and release

The actions of the objective compounds of the present invention on SRS-A production and release were determined in accordance with the method of Orange and Moore [J. Immunol., vol. 116, pp. 392 (1976)]. To lung fragments of guinea-pigs (male and female Hartley strain, weighing 300 to 350 g) sensitised with egg albumin as the antigen was added the objective compound of the present invention, simultaneously with the antigen, and the amount of SRS-A produced and released as a consequence was assayed by the method of Brocklehurst (J. Physiol., vol. 151, pp. 416–435, 1960). The results as shown in Table 1 indicate that the compounds of the present invention strongly inhibit the production and release of SRS-A in lower concentrations and that they are outstandingly excellent as compared with the known inhibitors of SRS-A production such as 5,7,11,14-eicosatetraynoic acid (ETYA) and sodium baicalein phosphate (BPS).

TABLE 1

The inhibitory action on SRS-A production and release

| Tested compound | Concentration ($\mu$M) | Inhibitory effect on SRS-A production (%) |
|---|---|---|
| Q–CH(CH₃)–…–COOH | 1 | 26.3 ± 11.3 |
| Q–…=…=…–OH | 10 | 78.9 ± 1.1 |
| Q–…≡…–OH | 1 | 21.5 ± 5.4 |
|  | 10 | 88.8 ± 5.7 |
| Q–…≡…≡…–OH | 10 | 74.7 ± 2.5 |
| Q–…≡…≡…–OH | 10 | 80.1 ± 3.1 |
| E–…=…–OH | 10 | 77.3 ± 1.4 |
| E–…≡…–OH | 1 | 15.7 ± 4.6 |
|  | 10 | 69.3 ± 7.1 |
| E–…≡…≡…–OH | 10 | 70.7 ± 10.4 |
| E–…≡…≡…–OH | 10 | 63 ± 7.2 |
| Q–…=…≡…–OH | 1 | 53.8 ± 6.3 |
|  | 10 | 77.7 ± 4.2 |
| K–…=…≡…–OH | 1 | 25.3 ± 8.7 |
|  | 10 | 61.6 ± 5.4 |
| Q–…=…≡…–OH | 1 | 20.2 ± 9.6 |
|  | 10 | 57.3 ± 12.7 |
| ETYA | 10 | 56.9 ± 5.9 |
| BPS | 100 | 50.8 ± 10.7 |

EXAMPLE 1

In a mixed solvent of acetonitrile (40 ml) and water (20 ml) were dissolved the compound produced in Reference Example 2 (II, $R^1=R^2=OCH_3$, $R^3=CH_3$, $m=0$, $n=4$, $X=-C\equiv C-$, $n'=3$, $Y^2=OH$, $k=1$, 3.00 g, 8.57 mmole) and 2,6-dicarboxypyridine N-oxide (4.70 g, 8.57×3 mmole), and the solution was stirred under cooling with ice. An ice-cooled solution of ceric ammonium nitrate (14.1 g, 8.57×3 mmole) in 50% aqueous acetonitrile (60 ml) was added dropwise to the solution over a period of 30 minutes, followed by stirring under the same conditions for 30 minutes and at room temperature for 30 minutes. After the completion of the reaction, insolubles were filtered out, and the acetonitrile was distilled off under reduced pressure. To the residue were added isopropyl ether (100 ml) and water (20 ml) for extraction, and the organic layer was washed with saturated sodium bicarbonate and aqueous sodium chloride successively, and dried (over MgSO₄), followed by distilling off the organic solvent under reduced pressure. The residue was chromatographed on a column of silica gel developing with isopropyl ether:ethyl acetate (98:2 to 95:5) to give 2,3-dimethoxy-5-methyl-6-(9-hydroxynon-5-ynyl)-1,4-benzoquinone (Ia, $R^1=OCH_3$, $m=0$, $n=4$, $X=-C\equiv C-$, $n'=3$, $k=1$, $Y^1=OH$, 2.24 g 82%). As to its physical properties, refer to Table 2 (The same shall apply hereinafter).

EXAMPLES 2 TO 15

By the procedure of Example 1, there were obtained the compounds as shown in Table 2.

EXAMPLE 16

In dioxane (10 ml) was dissolved the compound produced in Reference Example 5 (II, $R^1=R^3=CH_3$, $R^2=OCH_3$, $m=0$, $n=4$, $X=-C\equiv C-$, $n'=3$, $Y^2=OH$, $k=1$, 636 mg, 2.0 mmole). After silver oxide (AgO, 1.0 g, 8 mmole) was added to the solution, 6 N nitric acid (2.0 ml) was added to the mixture under stirring at room temperature, followed by allowing the reaction to proceed for 30 minutes. Water (50 ml) was added, and the product was extracted with ethyl acetate. The organic layer was washed with water, dried (over MgSO$_4$) and concentrated. The residue was chromatographed on silica gel developing with isopropyl ether:ethyl acetate (98:2) to give 2,3,5-trimethyl-6-(9-hydroxynon-5-ynyl)-1,4-benzoquinone (Ia, $R^1=CH_3$, $m=0$, $n=4$, $X=-C\equiv C-$, $n'=3$, $k=1$, $Y^1=OH$, 520 mg, 90%).

EXAMPLES 17 TO 20

By the procedure of Example 16, there were obtained the compounds as shown in Table 2.

EXAMPLE 21

In acetone (25 ml) was dissolved the compound produced in Reference Example 15 (II, $R^1=OCH_3$, $R^2=OCH_2OCH_3$, $R^3=CH_2OCH_3$, $m=1$, $n=1$, $X={}^H\!\!>=<^H$, $n'=4$, $k=1$, $Y^2=COOH$, 2.40 g, 5.0 mmole) and, after the addition of 2 N sulfuric acid (5.0 ml), the solution was stirred under reflux at 70° C. for 1 hour. After the reaction solution was cooled, 1 M aqueous ferric chloride solution (10.0 ml) was added, followed by stirring at room temperature for 30 minutes. After the completion of the reaction, the acetone was distilled off under reduced pressure, and the product was extracted by adding ethyl acetate (100 ml) and water (50 ml). The organic layer was washed with aqueous sodium chloride solution, dried (over MgSO$_4$) and concentrated. The residue was chromatographed on a column of silica gel developing with isopropyl ether:ethyl acetate (98:2) to give 2,3-dimethoxy-5-methyl-6-[11-carboxy-3-methyl-(E,Z)-2,6-undecadienyl]-1,4-benzoquinone (Ia, $R^1=OCH_3$, $m=1$, $n=1$, $X={}^H\!\!>=<^H$, $n'=4$, $k=1$, 2.17 g, 88%).

EXAMPLE 22

By the procedure of Example 21, there was obtained the compound as shown in Table 2.

EXAMPLE 23

In ethyl acetate (10 ml) was dissolved the compound produced in Example 7 (Ia, $R^1=CH_3$, $m=0$, $n=4$, $X=-C\equiv C-$, $n'=1$, $k=2$, $Y^1=OH$, 0.30 g, 1.0 mmole) and, after the Lindlar catalyst (60 mg) and quinoline (10 μl) were added to the solution, catalytic reduction was carried out at room temperature. At the time when 2.5 molar hydrogen was absorbed, the reaction was suspended. The catalyst was filtered out, and the ethyl acetate solution was washed with a 5% aqueous phosphoric acid solution (5 ml) and an aqueous sodium chloride solution (5 ml), successively, followed by concentrating the organic layer. The residue was dissolved in tetrahydrofuran (6 ml) and, after the addition of a 1 M aqueous ferric chloride solution, the mixture was stirred at room temperature for 30 minutes. The tetrahydrofuran was distilled off under reduced pressure, and the product was extracted by adding isopropyl ether (30 ml) and water (10 ml) to the residue. The organic layer was washed with aqueous sodium chloride, dried (over MgSO$_4$) and concentrated by distilling off the solvent under reduced pressure. The residue was chromatographed on a column of silica gel developing with isopropyl ether:ethyl acetate (98:2) to give 2,3,5-trimethyl-6-[10-hydroxy(Z,Z)-5,8-decadienyl]-1,4-benzoquinone (Ia, $R^1=CH_3$, $m=0$, $n=4$, $X={}^H\!\!>=<^H$, $n'=1$, $k=2$, $Y^1=OH$, 0.24 g, 80%).

EXAMPLES 24 TO 26

By the procedure of Example 23, there was obtained the compound as shown in Table 2.

EXAMPLE 27

In acetonitrile (10 ml) were dissolved the compound produced in Example 15 (Ia, $R^1=OCH_3$, $m=1$, $n=1$, $X={}^H\!\!>=<^H$, $n'=4$, $k=1$, $Y^1=COOH$, 0.78 g, 2.0 mmole) and N-hydroxysuccinimide (0.25 g, 2.2 mmole), and the solution was stirred under cooling with ice. After dicyclohexylcarbodiimide (0.45 g, 2.2 mmole) was added to the solution, the mixture was cooled with ice for 30 minutes and stirred at room temperature for 1.5 hours. Then, N-(3,4,5-trimethoxybenzyl)-piperazine (0.59 g, 2.2 mmole) was added, and the mixture was stirred at room temperature for 1 hour. After the completion of the reaction, dicyclohexyl urea was filtered out, and the acetonitrile was distilled off under reduced pressure. To the residue were added ethyl acetate (50 ml) and water (30 ml) for extraction, and the organic layer was washed with aqueous sodium bicarbonate solution and aqueous sodium chloride solution, successively, and dried (over MgSO$_4$), followed by distilling off the solvent. The residue was chromatographed on a column of silica gel developing with isopropyl ether:ethyl acetate (10:1) to give 2,3-dimethoxy-5-methyl-6-[[3-methyl-11-[N-((N'-(3,4,5-trimethoxybenzyl)-piperazinocarbonyl))-(E,Z)-2,6-undecadienyl]]]-1,4-benzoquinone (Ia, $R^1=OCH_3$, $m=1$, $n=1$, $X={}^H\!\!>=<^H$, $k=1$, $n'=4$,

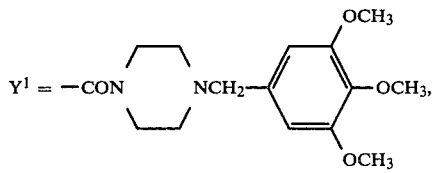

1.08 g, 85%).

EXAMPLES 28 TO 29

By the procedure of Example 27, there was obtained the compound as shown in Table 2.

EXAMPLE 30

In methanol (50 ml) was dissolved the compound produced in Reference Example 11 (II, $R^1=R^2=OCH_3$, $R^3=CH_3$, $m=1$, $n=2$, $X=-C\equiv C-$, $n'=2$, $k=1$,

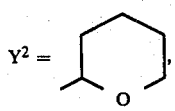

$Y^2 =$ 2.07 g, 3.98 mmole), and camphorsulfonic acid (0.1 g) was added to the solution, followed by refluxing for 1 hour. After the reaction solution was cooled, sodium bicarbonate (0.1 g) was added, and the solvent was distilled off under reduced pressure. The residue was dissolved in isopropyl ether (100 ml), and the organic layer was washed with water, dried (over magnesium sulfate) and concentrated under reduced pressure. The residue was chromatographed on silica gel developing with isopropyl ether:ethyl acetate (98:2) to give 2,3-dimethoxy-5-methyl-6-[10-hydroxy-3-methyl-7-yn-(2E)-decenyl]-1,4-hydrobenzoquinone (Ib, $R^1=OCH_3$, m=1, n=2, X=—C≡C—, n'=2, k=1, $Y^1=OH$, 1.29 g, 92%).

EXAMPLE 31

In a mixed solvent of acetonitrile (6 ml) and water (3 ml) were dissolved 5-methyl-1,2,3,4-tetramethoxy-6-(12-hydroxy-5,10-dodecadiynyl)benzene (II, 0.50 g, 1.29 mmole) and pyridine-2,6-dicarboxylic acid (0.65 g, 1.29×3 mmole), and the solution was stirred under cooling with ice, followed by adding dropwise and ice-cooled solution of ceric ammonium nitrate (2.12 g) in acetonitrile (4.5 ml) and water (4.5 ml) over a 15-minute period. The reaction was allowed to proceed under the same conditions for 15 minutes and further at room temperature for 15 minutes. After the completion of the reaction, the insolubles were filtered out, and the acetonitrile was distilled off under reduced pressure. By adding isopropyl ether (20 ml) and water (20 ml) to the residue, the product was extracted. The organic layer was washed with aqueous sodium bicarbonate solution and aqueous sodium chloride solution, successively, dried (over MgSO4) and concentrated under reduced pressure, resulting in a residue. The residue was chromatographed on a column of silica gel developing with a mixed solvent of isopropyl ether and ethyl acetate to give 2,3-dimethoxy-5-methyl-6-(12-hydroxy-5,10-dodecadiynyl)-1,4-benzoquinone (I, 0.42 g, 91%, oil).

EXAMPLE 32

Dioxane (15 ml) was added to 1,4-dimethoxy-2-methyl-3-[(12-hydroxy-5,10-dodecadiynyl)]naphthalene (II, 0.57 g, 1.5 mmole) and silver oxide (0.74 g, 6.0 mmole), and the mixture was stirred under cooling with ice. 6 N nitric acid (1.5 ml) was added to the mixture over a 5-minute period and, 5 minutes later, the ice bath was taken off, followed by stirring at room temperature for 30 minutes. Water (20 ml) was added to the reaction solution, and the dioxane was distilled off under reduced pressure. Ethyl acetate (50 ml) was added to the residue, and the insolubles were filtered out. The organic layer was separated out, washed with water and dried (over MgSO4), followed by distilling off the solvent under reduced pressure. The crystals precipitated were recrystallized from isopropyl ether, thereby yielding the desired 2-methyl-3-(12-hydroxy-5,10-dodecadiynyl)-1,4-naphthoquinone (I, 0.47 g, 90%).

EXAMPLES 33 TO 35

By the procedure of Example 31, there were obtained the compounds as shown in Table 2.

TABLE 2

| Ex. No. | Product | Starting material (Ref. Ex.) | Formula (M.W.) | NMR[in CDCl3, TMS internal standard, δ(ppm)] |
|---|---|---|---|---|
| 1 | Q~~~=~~~OH | 2 | $C_{18}H_{24}O_5$ (320.39) | 1.4–1.8(7H), 2.01(3H), 2.1–2.3(4H), 2.46(2H), 3.72(2H), 3.97(6H) |
| 2 | Q~~~=~~~=~~~OH | 3 | $C_{23}H_{30}O_5$ (386.49) | 1.4–1.8(9H), 2.01(3H), 2.1–2.3(8H), 2.46(2H), 3.72(2H), 3.96(6H) |
| 3 | Q~~~=~=~OH | 23 | $C_{19}H_{22}O_5$ (330.39) | 1.4–1.7(4H), 1.97(1H), 2.02(3H), 2.20(2H), 2.47(2H), 3.13(2H), 3.97(6H), 4.25(2H) |
| 4 | Q~~~=~=~OH | 24 | $C_{21}H_{26}O_5$ (358.44) | 1.4–1.9(7H), 2.02(3H), 2.1–2.4(4H), 2.47(2H), 3.07(2H), 3.72(2H), 3.97(6H) |
| 5 | Q~~~=~~~=~OH | 16 | $C_{23}H_{34}O_5$ (390.53) | 1.5–1.8(9H), 1.9–2.2 (8H), 2.00(3H), 2.45 (2H), 3.63(2H), 3.97 (6H), 5.3–5.5(4H) |
| 6 | E~~~=~~~OH | 14 | $C_{19}H_{28}O_3$ (304.43) | 1.3–1.7(9H), 1.9–2.2 (4H), 1.99(9H),2.47 (2H), 3.62(2H), 5.3–5.5(2H) |
| 7 | E~~~=~=~OH | 19 | $C_{19}H_{22}O_3$ (298.39) | 1.4–1.7(5H), 1.99(6H), 2.02(3H), 2.18(2H), 2.47(2H), 3.13(2H), 4.23(2H), m.p. 64–65° C. |

TABLE 2-continued

| Ex. No. | Product | Starting material (Ref. Ex.) | Formula (M.W.) | NMR [in CDCl$_3$, TMS internal standard, δ(ppm)] |
|---|---|---|---|---|
| 8 | E~≡≡~OH | 20 | C$_{20}$H$_{24}$O$_3$ (312.41) | 1.4–1.7(5H), 2.00(6H), 2.03(3H), 2.1–2.3(2H), 2.41(2H), 2.48(2H), 3.09(2H), 3.67(2H) |
| 9 | E~≡≡~OH | 21 | C$_{21}$H$_{26}$O$_3$ (326.44) | 1.4–1.9(7H), 2.00(6H), 2.03(3H), 2.1–2.3(4H), 2.48(2H), 3.07(2H), 3.73(2H) |
| 10 | E~≡≡~CN | 45 | C$_{22}$H$_{25}$NO$_2$ (335.45) | 1.4–1.9(6H), 2.0–2.3(4H), 2.05(6H), 2.08(3H), 2.3–2.7(4H), 3.15(2H), IR(neat): 2240 cm$^{-1}$ |
| 11 | E~=~COOH | 12 | C$_{19}$H$_{26}$O$_4$ (318.42) | 1.3–1.8(6H), 1.9–2.2(4H), 1.99(9H), 2.2–2.6(4H), 5.3–5.5(2H) |
| 12 | E~≡≡~COOH | 22 | C$_{22}$H$_{26}$O$_4$ (354.45) | 1.4–1.9(6H), 1.99(6H), 2.02(3H), 2.1–2.3(4H), 2.39(2H), 2.47(2H), 3.08(2H) |
| 13 | K(CH$_3$)$_2$~≡~COOH | 25 | C$_{29}$H$_{34}$O$_4$ (446.56) | 1.57(3H), 1.78(3H), 2.18(3H), 2.0–2.5(8H), 3.35(2H), 5.0(2H), 7.5–8.2(4H) |
| 14 | K(CH$_3$)$_2$~≡~OH | 7 | C$_{26}$H$_{30}$O$_3$ (390.50) | 1.57(3H), 1.78(3H), 2.18(3H), 2.0–2.5(8H), 3.35(2H), 4.24(2H), 5.0(2H), 7.5–8.2(4H) |
| 15 | Q(CH$_3$)$_2$~≡~OH | 8 | C$_{24}$H$_{32}$O$_5$ (400.50) | 1.57(3H), 1.72(3H), 2.0–2.5(8H), 3.97(6H), 4.23(2H), 5.0(2H) |
| 16 | E~≡~OH | 5 | C$_{18}$H$_{24}$O$_3$ (288.39) | 1.4–1.9(7H), 2.00(6H), 2.02(3H), 2.1–2.3(4H), 2.47(2H), 3.73(2H) |
| 17 | E~≡~≡~OH | 6 | C$_{21}$H$_{26}$O$_3$ (326.44) | 1.4–1.8(7H), 2.00(6H), 2.03(3H), 2.1–2.3(6H), 2.47(2H), 4.21(2H), m.p. 53–54° C. |
| 18 | E(CH$_3$)$_2$~≡~OH | 9 | C$_{24}$H$_{32}$O$_3$ (368.50) | 1.59(3H), 1.71(3H), 1.98(9H), 4.24(2H) |
| 19 | K(CH$_3$)~≡~OH | 10 | C$_{21}$H$_{22}$O$_3$ (322.39) | 1.78(3H), 2.18(3H), 3.35(2H), 4.23(2H), 5.0(1H), 7.5–8.2(4H) |
| 20 | K(CH$_3$)(≡)$_2$OH | 27 | C$_{23}$H$_{24}$O$_3$ (348.42) | 1.78(3H), 2.18(3H), 3.13(2H), 3.35(2H), 4.23(2H), 5.0(1H) |
| 21 | Q(CH$_3$)~=~COOH | 15 | C$_{22}$H$_{30}$O$_6$ (390.48) | 1.2–1.8(4H), 1.72(3H), 1.8–2.2(6H), 2.00(3H), 2.34(2H), 3.16(2H), 3.97(6H), 4.93(1H), 5.2–5.4(2H) |
| 22 | Q(CH$_3$)~≡~OH | 11 | C$_{20}$H$_{26}$O$_5$ (346.43) | 1.5–1.8(3H), 1.72(3H), 2.0–2.2(4H), 2.01(3H), 2.40(2H), 3.17(2H), 3.65(2H), 3.97(6H), 4.96(1H) |

TABLE 2-continued

| Ex. No. | Product | Starting material (Ref. Ex.) | Formula (M.W.) | NMR [in CDCl$_3$, TMS internal standard, δ(ppm)] |
|---|---|---|---|---|
| 23 | E~~~~~=~~OH | 7* | C$_{19}$H$_{26}$O$_3$ (302.42) | 1.3–1.6(4H), 1.8–2.2 (3H), 2.03(9H), 2.07 (3H), 2.50(2H), 2.84 (2H), 4.26(2H), 5.3–5.8(4H) |
| 24 | Q~~~=~=~~OH | 4* | C$_{21}$H$_{30}$O$_5$ (362.47) | 1.3–1.8(7H), 1.9–2.3 (4H), 2.00(3H), 2.46 (2H), 2.78(2H), 3.64 (2H), 3.97(6H), 5.3–5.5(4H) |
| 25 | Q~~~(=)$_3$~OH | 26 | C$_{22}$H$_{30}$O$_5$ (374.46) | 1.3–1.8(4H), 1.9–2.3 (4H), 2.00(3H), 2.5–2.85(4H), 3.97(6H), 4.26(2H), 5.3–5.8 (6H) |
| 26 | K~~=(CH$_3$)~~(=)$_2$~OH | 18 | C$_{24}$H$_{28}$O$_3$ (364.46) | 1.78(3H), 2.18(3H), 2.4–2.6(4H), 2.85(2H), 3.35(2H), 4.25(2H), 5.0(1H), 5.3–5.8(4H), 7.5–8.2(4H) |
| 27 | Q~O~=~CH$_3$~=~~C(O)N(piperazine)NCH$_2$(3,4,5-trimethoxyphenyl) | 21* | C$_{36}$H$_{50}$N$_2$O$_8$ (638.81) | 1.2–1.8(4H), 1.72(3H), 1.9–2.5(12H), 2.00 (3H), 3.16(2H), 3.4–3.7(4H), 3.42(2H), 3.84(9H), 3.97(6H), 4.93(1H), 5.2–5.4(2H), 6.53(2H) |
| 28 | E~~~≡~≡~~C(O)NH–CH(CH$_3$)$_2$ | 12* | C$_{25}$H$_{38}$NO$_3$ (395.55) | 1.13(3H), 1.24(3H), 1.4–2.0(6H), 2.0–2.4 (6H), 2.05(6H), 2.08 (3H), 2.53(2H), 3.14 (2H), 4.0–4.4(1H), 5.5–5.7(1H) |
| 29 | E~~~~=~~CONH$_2$ | 11* | C$_{18}$H$_{25}$NO$_3$ (303.39) | 1.3–1.7(6H), 1.9–2.2 (4H), 1.99(9H), 2.47 (2H), 5.3–5.5(2H) |
| 30 | Q$_1$~=(CH$_3$)~~≡~~OH | 11 | C$_{20}$H$_{28}$O$_5$ (348.45) | 1.4–1.9(3H), 1.77(3H), 1.9–2.6(6H), 2.16(3H), 3.37(2H), 3.71(2H), 3.93(6H), 5.18(1H), 5.74(1H), 5.79(1H) |
| 31 | Q~~~≡~≡~~OH | 46 | C$_{21}$H$_{26}$O$_5$ (358.44) | 1.4–1.8(7H), 2.1–2.4 (6H), 2.03(3H), 2.47 (2H), 3.97(6H), 4.22 (2H) |
| 32 | K~~~≡~≡~~OH | 47 | C$_{23}$H$_{24}$O$_3$ (348.45) | 1.5–1.8(6H), 1.81(1H), 2.1–2.4(6H), 2.20(3H), 2.64(2H), 4.20(2H), 7.6–7.8(2H), 8.0–8.2 (2H), m.p. 97–98° C. |
| 33 | Q~~~=~=~~OH | 48 | C$_{21}$H$_{30}$O$_5$ (362.47) | 1.2–1.7(7H), 1.9–2.3 (6H), 2.00(3H), 2.44 (2H), 3.97(6H), 4.0–4.2(2H), 5.3–5.6(4H) |
| 34 | K~~~=~=~~OH | 49 | C$_{23}$H$_{28}$O$_3$ (352.48) | 1.2–1.7(7H), 1.9–2.3 (6H), 2.18(3H), 2.63 (2H), 4.0–4.2(2H), 5.3–5.6(4H), 7.6–7.8 (2H), 8.0–8.2(2H) |

TABLE 2-continued

| Ex. No. | Product | Starting material (Ref. Ex.) | Formula (M.W.) | NMR[in CDCl$_3$, TMS internal standard, δ(ppm)] |
| --- | --- | --- | --- | --- |
| 35 | 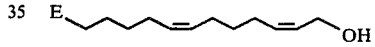 | 50 | C$_{21}$H$_{30}$O$_3$ (330.47) | 1.2–1.6(7H), 1.8–2.2 (6H), 2.01(9H), 2.48 (2H), 4.0–4.2(2H), 5.3–5.6(4H) |

Note:
The Number marked by * means Example No.

The following reference examples illustrate the production of the starting compounds utilized in the above examples.

REFERENCE EXAMPLE 1

A solution of tetrahydropyranyl ether of propargyl alcohol (16.8 g, 0.12 mmole) in ether (15 ml) was added dropwise to the freshly prepared sodium amide (2.88 g of sodium and 50 mg of ferric nitrate) in liquid ammonia (300 ml) under argon atmosphere at −60° C. to −40° C. over a 20-minute period, and the mixed solution was stirred under the same conditions for 40 minutes. A solution of the compound produced in Reference Example 29 (IV, R$^1$=R$^2$=OCH$_3$, R$^3$=CH$_3$, m=0, n=4, Z=I, 39.4 g, 0.10 mole) in ether (40 ml) was added dropwise to the reaction solution at −60° to −50° C. over a 40-minute period, followed by stirring under the same conditions for 1 hour. Ammonium chloride (50 g) was added to the reaction solution, and ammonia was removed under reduced pressure. Then, isopropyl ether (300 ml) and water (300 ml) were added, and the product was extracted. The organic layer was washed with two portions of saturated aqueous ammonia (300 ml) and dried (over MgSO$_4$), and the solvent was distilled off, leaving a residue. The residue was dissolved in methanol (300 ml), and p-toluenesulfonic acid (0.95 g) was added, followed by stirring at 70° C. for 0.5 hour. After the solution was cooled, aqueous sodium bicarbonate solution (50 ml) was added, and the methanol was distilled off under reduced pressure. To the residue were added isopropyl ether (300 ml) and water (200 ml) for extraction. The organic layer was washed with an aqueous sodium chloride solution and dried (over MgSO$_4$), and the solvent was distilled off under reduced pressure. The residue was chromatographed on a column of silica gel developing with isopropyl ether-:ethyl acetate (49:1) to give 1,2,3,4-tetramethoxy-5-methyl-6-(7-hydroxy-5-heptynyl)benzene (II, R$^1$=R$^2$=OCH$_3$, R$^3$=CH$_3$, m=0, n=4, X=—C≡C—, n'=1, k=1, Y$^2$=OH, 27.4 g, 85%). As to the physical properties, see Table 3 (the same shall apply hereinafter).

REFERENCE EXAMPLES 2 TO 10

By the procedure of Reference Example 1, there were obtained the compounds as shown in Table 3.

REFERENCE EXAMPLE 11

In the same manner as in Reference Example 1, 2,3-dimethoxy-1,4-bismethoxymethyloxy-5-methyl-6-(6-iodo-3-methyl-2-hexenyl)-benzene (IV, R$^1$=OCH$_3$, R$^2$=OCH$_2$OCH$_3$, R$^3$=CH$_2$OCH$_3$, m=1, n=2, Z$^1$=I, 2.37 g, 4.8 mmole) produced in Reference Example 28 was allowed to undergo the coupling reaction with 2-tetrahydropyranyl ether of 3-butyn-1-ol (0.96 g, 5.3 mmole) in the presence of sodium amide (0.14 g as sodium) in liquid ammonia (30 ml). After the completion of the reaction, ammonium chloride (5 g) was added, and the ammonia was removed under reduced pressure. Water was added to the residue, and the product was extracted with isopropyl ether (100 ml). The organic layer was washed with water, dried and concentrated under reduced pressure. The residue was chromatographed on a column of silica gel developing with isopropyl ether to give 2,3-dimethoxy-1,4-bismethoxymethyloxy-5-methyl-6-[10-(2-tetrahydropyranyloxy)-3-methyl-7-yn-2-decenyl)benzene (II, R$^1$=OCH$_3$, R$^2$=OCH$_2$OCH$_3$, R$^3$=—CH$_2$OCH$_3$, m=1, n=2, k=1, X=—C≡C—, n'=2, Y$^2$ = 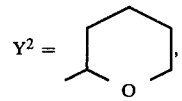, 2.07 g, 83%).

REFERENCE EXAMPLE 12

Anhydrous dimethyl sulfoxide (12 ml) was added to sodium hydride (1.44 g, 60 mmole) in an atmosphere of argon, and the mixture was stirred at 65° to 70° C. for 1 hour. After cooling at 10° to 15° C., a solution of 5-carboxypentyltriphenylphosphonium bromide (VIII, n'=5, Y$^2$=COOH, 13.7 g, 30 mmole) in anhydrous dimethyl sulfoxide (70 ml) was added dropwise to the mixture over a 30-minute period, followed by stirring under cooling with water for 15 minutes. A solution of 2,3,5-trimethyl-1,4-dimethoxy-6-(3-formylpropyl)-benzene (V, R$^1$=R$^3$=CH$_3$, R$^2$=OCH$_3$, m=0, n=4, 5.0 g, 20 mmole) produced in Reference Example 44 in dimethyl sulfoxide (20 ml) was added dropwise to the mixture over a 20-minute period, followed by stirring at room temperature for 40 minutes. After the completion of the reaction, 10% aqueous phosphoric acid solution (40 ml), isopropyl ether (250 ml) and water (150 ml) were added successively, and the product was extracted. The organic layer was washed with aqueous sodium chloride solution, dried (over MgSO$_4$) and concentrated. Then, the residue was chromatographed on a column of silica gel developing with isopropyl ether-:ethyl acetate (98:2) to give 2,3,5-trimethyl-1,4-dimethoxy-6-(9-carboxy-(4Z)-nonenyl)-benzene (II, R$^1$=R$^3$=CH$_3$, R$^2$=OCH$_3$, m=0, k=1, n=4, X=$^H$>×<$^H$, n'=5, Y$^2$=COOH, 5.66 g, 81%).

REFERENCE EXAMPLES 13 TO 15

By the procedure of Reference Example 12, there were produced the compounds as shown in Table 3.

REFERENCE EXAMPLE 16

In ethyl acetate (10 ml) was dissolved 1,2,3,4-tetramethoxy-5-methyl-6-(12-hydroxy-5,8-dodecadiynyl)-benzene (II, 500 mg, 1.2 mmole) produced in Reference Example 24, and, after the addition to the solution of the Lindlar catalyst (48 mg) and quinoline (7 µl), hydrogenation was carried out at room temperature. At the time when the theoretical amount of hydrogen was absorbed, the reaction was suspended, and the catalyst was removed, followed by distilling off the solvent under reduced pressure. The residue was chromatographed on a column of silica gel, developing with isopropyl ether to give 1,2,3,4-tetramethoxy-5-methyl-6-(12-hydroxy-(5Z,8Z)-dodecadienyl)-benzene (II, 470 mg, 93%)

REFERENCE EXAMPLES 17 TO 18

By the procedure of Reference Example 16, there were produced the compounds as shown in Table 3.

REFERENCE EXAMPLE 19

A tetrahydrofuran solution of 2,3,5-trimethyl-1,4-dimethoxy-6-(7-iodohept-5-ynyl)-benzene (II-1a, $R^1=R^3=CH_3$, $R^2=OCH_3$, m=0, n=4, X=—C≡C—, k=1, n'=1, Z=I, 4.00 g, 10 mmole) obtained in Reference Example 33 was added dropwise over a 20-minute period to a solution of Grignard reagent in tetrahydropyran ether of propargyl alcohol prepared in advance in an atmosphere of argon [which was prepared by reaction of ethylmagnesium bromide in tetrahydrofuran (50 ml) under argon, prepared from magnesium (0.27 g) and ethyl bromide (1.31 g), adding a solution of tetrahydropyranyl ether of propargyl alcohol (1.56 g) in tetrahydrofuran (5 ml) over a 20-minute period, stirring the mixture at 50° C. for 1 hour, cooling the reaction solution to room temperature, adding cuprous bromide (30 mg) and stirring at room temperature for 15 minutes], and the mixture was stirred at 50° C. for 2 hours. The reaction solution was cooled, after the completion of the reaction, and aqueous ammonium chloride solution (30 ml) was added, followed by stirring. The tetrahydrofuran was distilled off under reduced pressure, and the product was extracted with isopropyl ether (50 ml). The organic layer was washed with aqueous ammonium chloride solution (30 ml) and dried (over MgSO₄), and the solvent was distilled off. The residue was dissolved in methanol (50 ml), and p-toluenesulfonic acid (0.1 g) was added, followed by heating at 70° C. Following the cooling, aqueous sodium bicarbonate solution (20 ml) was added, and the methanol was distilled off under reduced pressure. Isopropyl ether (100 ml) and water (50 ml) were added to the residue, and the product was extracted. The organic layer was washed with aqueous sodium chloride solution and dried (over MgSO₄), and the solvent was distilled off under reduced pressure. The residue was chromatographed on a column of silica gel developing with isopropyl ether to give 2,3,5-trimethyl-1,4-dimethoxy-6-(10-hydroxydeca-5,8-diynyl)-benzene (II, $R^1=R^3=CH_3$, $R^2=OCH_3$, m=0, n=4, X=—C≡C—, n'=1, k=2, $Y^2$=OH, 2.44 g, 74%).

REFERENCE EXAMPLES 20 TO 27

By the procedure of Reference Example 19, there were obtained the compounds as shown in Table 3.

REFERENCE EXAMPLE 28

In methylene chloride (250 ml) were dissolved 2,3,5-trimethyl-1,4-dimethoxy-6-(4-hydroxybutyl)-benzene (VI, $R^1=R^3=CH_3$, $R^2=OCH_3$, m=0, n=4, 26.1 g, 0.104 mole) and triethylamine (21.8 ml, 0.104×1.5 mole), and the solution was stirred under cooling with ice. A solution of methanesulfonyl chloride (14.3 g, 0.104×1.2 mole) in methylene chloride (30 ml) was added dropwise to the solution over a 30-minute period, followed by stirring under cooling with ice for 30 minutes. After the completion of the reaction, the organic layer was washed with ice water (250 ml), 10% aqueous, cold hydrochloric acid (250 ml), aqueous saturated sodium bicarbonate solution (250 ml) and aqueous sodium chloride solution (250 ml), successively, dried (over MgSO₄) and concentrated. The residual solution was dissolved in acetone (300 ml), to which sodium iodide (39.0 g) was added, and the reaction was allowed to proceed at 50° C. for 2 hours. After the completion of the reaction, the acetone was distilled off under reduced pressure, and to the residue were added isopropyl ether (300 ml) and H₂O (200 ml) for extraction of the product. The organic layer was washed with 5% aqueous sodium hydrosulfite solution (200 ml) and aqueous sodium chloride solution (200 ml), successively, and dried (over MgSO₄), followed by distilling off the solvent. The residue was chromatographed on a column of silica gel developing with a mixed solvent of hexane:isopropyl ether (3:1 to 2:1) to give 2,3,5-trimethyl-1,4-dimethoxy-6-(4-iodobutyl)benzene (IV, $R^1=R^3=CH_3$, $R^2=OCH_3$, m=0, n=4, Z=I, 35.3 g, 94%).

REFERENCE EXAMPLES 29 TO 41

By the procedure of Reference Example 28, there were obtained the products as shown in Table 3.

REFERENCE EXAMPLE 42

In anhydrous dimethyl sulfoxide (75 ml) were dissolved 1,2,3,4-tetramethoxy-5-methyl-6-(4-hydroxybutyl)benzene (VI, $R^1=R^2=OCH_3$, $R^3=CH_3$, m=0, n=4, 14.2 g, 50 mmole) and triethylamine (56.0 ml), and the solution was stirred at room temperature. A solution of sulfur trioxide pyridine complex (31.8 g, 200 mmole) in anhydrous dimethyl sulfoxide (75 ml) was added dropwise to the solution over a 25-minute period, followed by stirring at room temperature for 35 minutes. The reaction solution was poured into ice-water (300 g), and the product was extracted with isopropyl ether (500 ml). The isopropyl ether layer was washed with 10% aqueous phosphoric acid solution and aqueous sodium chloride solution, successively, and dried (over MgSO₄), and the solvent was distilled off. The residue was distilled under reduced pressure, thereby yielding 1,2,3,4-tetramethoxy-5-methyl-6-(3-formylpropyl)-benzene (V, $R^1=R^2=OCH_3$, $R^3=CH_3$, m=0, n=4, 11.3 g, 80%, bp$_{0.7}$ 137° to 140° C.).

REFERENCE EXAMPLES 43 TO 44

By the procedure of Reference Example 42, there were obtained the compounds as shown in Table 3.

REFERENCE EXAMPLE 45

In dimethyl sulfoxide (4 ml) was dissolved 2,3,5-trimethyl-1,4-dimethoxy-6-(12-iodo-5,8-dodecadiynyl)-benzene (0.47 g, 1.0 mmole) produced in Reference Example 35, and sodium cyanide (98 mg, 2.0 mmole) was added, followed by stirring at room temperature for 1 hour. Ether (20 ml) and water (10 ml) were added for extraction of the product. The organic layer was washed with aqueous sodium chloride solution and dried (over MgSO$_4$), and the solvent was distilled off. The residue was chromatographed on a column of silica gel developing with isopropyl ether to give 2,3,5-trimethyl-1,4-dimethoxy-6-(12-cyano-5,8-dodecadiynyl)-benzene (II, 0.24 g, 66%).

REFERENCE EXAMPLE 46

Sodium amide (1.01 g, 20.0×1.3 mmole) was suspended in anhydrous tetrahydrofuran (10 ml), and the suspension was stirred under a stream of nitrogen at room temperature, followed by adding dropwise a solution of 1-(2-tetrahydropyranyloxy)-2,7-octadiyne (4.12 g, 20.0 mmole) in anhydrous tetrahydrofuran over a 30-minute period. Following the dropwise addition, the reaction temperature was increased to 50° C., and the reaction was conducted under stirring for 1.5 hours. The reaction mixture was cooled with ice and, after the addition of hexamethylphosphoramide (5 ml), a solution of 5-methyl-1,2,3,4-tetramethoxy-6-[1-(4-iodobutyl)]-benzene (7.88 g, 20.0 mmole) in anhydrous tetrahydrofuran (20 ml) was added dropwise over a 30-minute period, followed by stirring under the same conditions for 30 minutes and then at room temperature for 1 hour. To the reaction mixture were added ammonium chloride (1.4 g) and water (20 ml) for decomposition of excess reagents. Tetrahydrofuran was distilled off under reduced pressure, and to the residue were added isopropyl ether (100 ml) and water (50 ml) for extraction of the product. The organic layer was washed with aqueous sodium chloride solution and dried (over MgSO$_4$), and the solvent was removed under reduced pressure. The residue was dissolved in methanol (40 ml), and p-toluenesulfonic acid (0.19 g) was added, followed by stirring at 70° C. for 30 minutes. After the cooling, sodium bicarbonate (1 g) was added, and the mixture was concentrated under reduced pressure. To the residue were added isopropyl ether (100 ml) and water (50 ml) for extraction of the product. The organic layer was washed with aqueous sodium chloride solution, dried (over MgSO$_4$) and concentrated under reduced pressure. The residue was chromatographed on a column of silica gel developing with an isopropyl ether hexane mixed solvent to give 5-methyl-1,2,3,4-tetramethoxy-6-(12-hydroxy-5,10-dodecadiynyl)benzene (5.33 g, 75%, oil).

REFERENCE EXAMPLE 47

By condensing 1,4-dimethoxy-2-methyl-3-(4-iodobutyl)naphthalene (3.84 g, 10 mmole) with 1-(2-tetrahydropyranyloxy)-2,7-octadiyne (2.10 g, 10 mmole) in accordance with the procedure of the above Reference Example 46, there was produced 1,4-dimethoxy-2-methyl-3-(12-hydroxy-5,10-dodecadiynyl)naphthalene (2.78 g, 73.5%, oily product). 1,4-Dimethoxy-2-methyl-3-(4-iodobutyl)naphthalene [δ1.5 to 2.2(4H), 2.40(3H), 2.82(2H), 3.23(2H), 3.84(3H), 3.87 (3H), 7.3 to 7.5(2H), 7.8 to 8.1(2H)] as utilized in this Reference Example was produced from 1,4-dimethoxy-2-methyl-3-(4-hydroxybutyl)naphthalene [oily substance, NMR (CDCl$_3$), δ1.5 to 1.8(5H), 2.39(3H), 2.81(2H), 3.67(2H), 3.84(3H), 3.87(3H), 7.3 to 7.5(2H), 7.9 to 8.1(2H)] in accordance with the procedure described in Japanese Patent Application No. 49433/'80.

REFERENCE EXAMPLES 48 TO 50

By partially reducing with the Lindlar catalyst the compounds containing triple bond produced in the above Reference Examples 6, 46 and 47 in accordance with Reference Example 16, there were produced the corresponding compounds (see Table 3).

TABLE 3

| Ref. Ex. | Product | Starting material (Ref. Ex.) | Formula (M.W.) | NMR[in CDCl$_3$, TMS internal standard, δ(ppm)] |
|---|---|---|---|---|
| 1 | Q$_2$~~~=~~OH | 29 | C$_{18}$H$_{26}$O$_5$ (322.41) | 1.4–1.7(4H), 1.81(1H), 2.16(3H), 2.26(2H), 2.57(2H), 3.76(3H), 3.80(3H), 3.87(6H), 4.22(2H) |
| 2 | Q$_2$~~~~=~~~OH | 29 | C$_{20}$H$_{30}$O$_5$ (350.46) | 1.4–1.8(7H), 2.1–2.3 (4H), 2.16(3H), 2.56 (2H), 3.71(2H), 3.76 (3H), 3.80(3H), 3.88 (6H) |
| 3 | Q$_2$~~~~=~~~=~~OH | 31 | C$_{25}$H$_{36}$O$_5$ (416.56) | 1.4–2.0(9H), 2.1–2.4 (8H), 2.21(3H), 2.63 (3H), 3.71(2H), 3.87 (3H), 3.91(3H), 3.99 (6H) |
| 4 | E$_1$~~~=~~OH | 32 | C$_{18}$H$_{26}$O$_3$ (290.41) | 1.5–1.7(4H), 1.77(1H), 2.1–2.3(2H), 2.16(6H), 2.20(3H), 2.60(2H), 3.62(3H), 3.64(3H), 4.19(2H): m.p. 65–66° C. |
| 5 | E$_1$~~~~=~~~OH | 32 | C$_{20}$H$_{30}$O$_3$ (318.46) | 1.5–1.8(7H), 2.1–2.3 (4H), 2.16(6H), 2.20 (3H), 2.60(2H), 3.62 (3H), 3.64(3H), 3.71 (2H) |

TABLE 3-continued

| Ref. Ex. | Product | Starting material (Ref. Ex.) | Formula (M.W.) | NMR[in CDCl$_3$, TMS internal standard, δ(ppm)] |
|---|---|---|---|---|
| 6 | 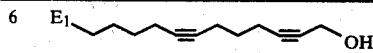 | 34 | C$_{23}$H$_{32}$O$_3$ (356.51) | 1.4–2.0(7H), 2.1–2.4 (6H), 2.20(6H), 2.25 (3H), 2.64(2H), 3.69 (3H), 3.72(3H), 4.24 (2H) |
| 7 | 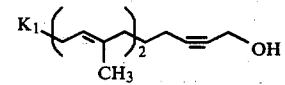 | 40 | C$_{28}$H$_{36}$O$_3$ (420.57) | 1.56(3H), 1.84(3H), 2.33(3H), 3.82(6H), 4.22(2H), 5.1(2H), 7.2–8.2(4H) |
| 8 | 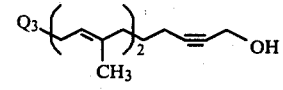 | 37 | C$_{28}$H$_{42}$O$_7$ (490.62) | 1.62(3H), 1.79(3H), 1.9–2.5(6H), 2.20(3H), 3.25(2H), 3.62(3H), 3.64(3H), 3.92(6H), 4.23(2H), 5.13(4H), 5.1(2H) |
| 9 | 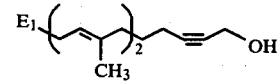 | 38 | C$_{26}$H$_{38}$O$_3$ (398.56) | 1.61(3H), 1.76(3H), 1.8–2.4(6H), 2.16(3H), 3.20(2H), 3.68(3H), 3.70(3H), 4.23(2H), 5.1(2H) |
| 10 | 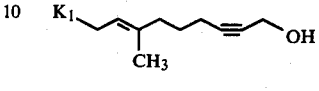 | 39 | C$_{23}$H$_{28}$O$_3$ (352.45) | 1.86(3H), 2.33(3H), 1.8–2.2(4H), 3.35(2H), 3.48(2H), 3.81(6H), 4.22(2H), 5.1(1H), 7.2–8.2(4H) |
| 11 | 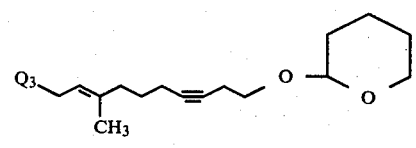 | 28 | C$_{29}$H$_{44}$O$_8$ (520.64) | 1.62(3H), 1.79(3H), 2.20(3H), 3.24(2H), 3.4–4.1(4H), 3.62(3H), 3.64(3H), 3.92(6H), 4.72(1H), 5.0(1H), 5.13(4H) |
| 12 |  | 44 | C$_{21}$H$_{32}$O$_4$ (348.49) | 1.3–1.8(6H), 1.9–2.3 (4H), 2.16(6H), 2.20 (3H), 2.35(2H), 2.62 (2H), 3.62(3H), 3.65 (3H), 5.3–5.5(2H) |
| 13 | 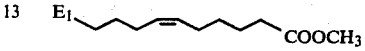 | 44 | C$_{22}$H$_{34}$O (362.51) | 1.3–1.8(6H), 1.9–2.2 (4H), 2.16(6H), 2.20 (3H), 2.32(2H), 2.61 (2H), 3.62(3H), 3.65 (6H), 5.3–5.5(2H) |
| 14 |  | 44 | C$_{21}$H$_{34}$O$_3$ (334.50) | 1.3–1.7(9H), 1.9–2.2 (4H), 2.16(6H), 2.20 (3H), 2.61(2H), 3.60 (2H), 3.62(3H), 3.64 (3H), 5.3–5.5(2H) |
| 15 | 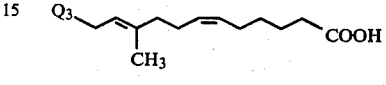 | 43 | C$_{26}$H$_{40}$O$_8$ (480.61) | 1.2–1.8(4H), 1.75(3H), 1.8–2.2(6H), 2.16(3H), 2.33(2H), 3.36(2H), 3.56(3H), 3.58(3H), 3.85(6H), 4.9–5.1(1H), 5.04(4H), 5.2–5.4(2H) |
| 16 |  | 24 | C$_{23}$H$_{36}$O$_5$ (392.54) | 1.3–1.9(7H), 1.9–2.3 (4H), 2.19(3H), 2.62 (2H), 2.84(2H), 3.71 (2H), 3.85(3H), 3.89 (3H), 3.98(6H), 5.4–5.6(4H) |
| 17 | 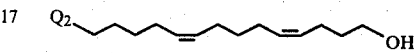 | 3 | C$_{25}$H$_{40}$O$_5$ (420.60) | 1.3–1.8(9H), 1.9–2.3 (8H), 2.21(3H), 2.62 (2H), 3.72(2H), 3.85 (3H), 3.89(3H), 3.99 (6H), 5.4–5.6(4H) |

TABLE 3-continued

| Ref. Ex. | Product | Starting material (Ref. Ex.) | Formula (M.W.) | NMR [in CDCl$_3$, TMS internal standard, δ(ppm)] |
|---|---|---|---|---|
| 18 | K$_1$—CH=C(CH$_3$)—CH$_2$CH$_2$CH$_2$—CH=CH—(CH$_2$)$_2$OH | 7 | C$_{26}$H$_{34}$O$_3$ (394.53) | 1.86(3H), 2.33(3H), 2.0–2.5(6H), 2.85(2H), 3.50(2H), 3.81(6H), 4.26(2H), 5.0–5.8(5H), 7.2–8.2(4H) |
| 19 | E$_1$—(CH$_2$)$_n$—C≡C—C≡C—CH$_2$OH | 33 | C$_{21}$H$_{28}$O$_3$ (328.46) | 1.5–1.7(5H), 2.1–2.3(2H), 2.16(6H), 2.20(3H), 2.60(2H), 3.13(2H), 3.62(3H), 3.64(3H), 4.20(2H) |
| 20 | E$_1$—(CH$_2$)$_n$—C≡C—C≡C—CH$_2$CH$_2$OH | 33 | C$_{22}$H$_{30}$O$_3$ (342.48) | 1.5–1.7(4H), 1.92(1H), 2.1–2.3(2H), 2.16(6H), 2.21(3H), 2.41(2H), 2.60(2H), 3.09(2H), 3.62(3H), 3.64(3H), 3.66(2H) |
| 21 | E$_1$—(CH$_2$)$_n$—C≡C—C≡C—(CH$_2$)$_3$OH | 33 | C$_{23}$H$_{32}$O$_3$ (356.51) | 1.5–2.0(7H), 2.1–2.3(4H), 2.16(6H), 2.20(3H), 2.60(2H), 3.07(2H), 3.62(3H), 3.64(3H), 3.70(2H) |
| 22 | E$_1$—(CH$_2$)$_n$—C≡C—C≡C—(CH$_2$)$_3$COOH | 33 | C$_{24}$H$_{32}$O$_4$ (384.52) | 1.5–1.9(6H), 2.1–2.3(4H), 2.15(6H), 2.20(3H), 2.46(2H), 2.60(2H), 3.07(2H), 3.62(3H), 3.64(3H) |
| 23 | Q$_2$—(CH$_2$)$_n$—C≡C—C≡C—CH$_2$OH | 30 | C$_{21}$H$_{28}$O$_5$ (360.46) | 1.4–1.8(4H), 1.94(1H), 2.1–2.3(2H), 2.16(3H), 2.57(2H), 3.14(2H), 3.76(3H), 3.80(3H), 3.87(6H), 4.22(2H) |
| 24 | Q$_2$—(CH$_2$)$_n$—C≡C—C≡C—(CH$_2$)$_3$OH | 30 | C$_{23}$H$_{32}$O$_5$ (388.51) | 1.4–1.9(7H), 2.1–2.4(4H), 2.16(3H), 2.57(2H), 3.06(2H), 3.70(2H), 3.76(3H), 3.80(3H), 3.87(6H) |
| 25 | K$_1$—[CH=C(CH$_3$)—CH$_2$CH$_2$]$_2$—C≡C—(CH$_2$)$_3$COOH | 40 | C$_{13}$H$_{40}$O$_4$ (476.63) | 1.55(3H), 1.83(3H), 2.33(3H), 3.50(2H), 3.81(6H), 5.05(2H), 7.2–8.2(4H) |
| 26 | Q$_2$—(CH$_2$)$_n$—(CH=CH)$_3$—OH | 36 | C$_{24}$H$_{30}$O$_5$ (398.48) | 1.4–1.8(4H), 1.90(1H), 2.1–2.3(2H), 2.16(3H), 2.58(2H), 3.14(2H), 3.20(2H), 3.76(3H), 3.80(3H), 3.87(6H), 4.23(2H) |
| 27 | K$_1$—CH=C(CH$_3$)—CH$_2$CH$_2$—C≡C—(CH$_2$)$_2$OH | 41 | C$_{26}$H$_{32}$O$_3$ (392.52) | 1.86(3H), 2.33(3H), 1.8–2.4(4H), 2.40(2H), 3.15(2H), 3.50(2H), 3.81(6H), 5.1(1H), 7.2–8.2(4H) |
| 28 | E$_1$—(CH$_2$)$_n$—I | — | C$_{15}$H$_{23}$O$_2$I (362.25) | 1.4–1.7(2H), 1.91(2H), 2.16(6H), 2.20(3H), 2.61(2H), 3.20(2H), 3.62(3H), 3.64(3H) |
| 29 | Q$_2$—(CH$_2$)$_n$—I | — | C$_{15}$H$_{23}$O$_4$I (394.25) | 1.4–1.7(2H), 1.90(2H), 2.15(3H), 2.59(2H), 3.20(2H), 3.76(3H), 3.80(3H), 3.87(6H) |
| 30 | Q$_2$—(CH$_2$)$_n$—C≡C—CH$_2$I | — | C$_{18}$H$_{25}$O$_4$I (432.30) | 1.4–1.8(4H), 2.20(3H), 2.2–2.4(2H), 2.61(2H), 3.75(2H), 3.83(3H), 3.88(3H), 3.95(6H) |

TABLE 3-continued

| Ref. Ex. | Product | Starting material (Ref. Ex.) | Formula (M.W.) | NMR [in CDCl$_3$, TMS internal standard, δ(ppm)] |
|---|---|---|---|---|
| 31 | Q$_2$–≡–I | — | C$_{20}$H$_{29}$O$_4$I (460.36) | 1.4–1.8(6H), 1.9–2.4 (4H), 2.19(3H), 2.60 (2H), 3.29(2H), 3.81 (3H), 3.85(3H), 3.92 (6H) |
| 32 | Q$_3$–=–I (CH$_3$) | — | C$_{20}$H$_{31}$O$_6$I (494.37) | 1.79(3H), 1.9–2.3(4H), 2.20(3H), 3.26(2H), 3.42(2H), 3.62(3H), 3.64(3H), 3.91(6H), 5.13(4H), 5.18(1H) |
| 33 | E$_1$–≡–I | — | C$_{18}$H$_{25}$O$_2$I (400.30) | 1.5–1.7(4H), 2.1–2.3 (2H), 2.16(6H), 2.20 (3H), 2.60(2H), 3.62 (3H), 3.64(3H), 3.66 (2H) |
| 34 | E$_1$–≡–I | — | C$_{20}$H$_{29}$O$_2$I (428.36) | 1.4–1.8(6H), 1.9–2.4 (4H), 2.21(6H), 2.26 (3H), 2.65(2H), 3.34 (2H), 3.71(3H), 3.73 (3H) |
| 35 | E$_1$–≡–≡–I | — | C$_{23}$H$_{31}$O$_2$I (466.41) | 1.5–1.8(4H), 1.8–2.4 (6H), 2.23(6H), 2.27 (3H), 2.67(2H), 3.16 (2H), 3.34(2H), 3.72 (3H), 3.74(3H) |
| 36 | Q$_2$–(≡)$_2$–I | — | C$_{21}$H$_{27}$O$_4$I (470.35) | 1.4–1.8(4H), 2.20(3H), 2.0–2.4(2H), 2.62(2H), 3.21(2H), 3.76(2H), 3.81(3H), 3.85(3H), 3.92(6H) |
| 37 | Q$_3$–(=)$_2$–I (CH$_3$) | — | C$_{25}$H$_{39}$O$_6$I (562.48) | 1.62(3H), 1.79(3H), 1.9–2.4(6H), 2.20(3H), 3.26(2H), 3.43(2H), 3.62(3H), 3.64(3H), 3.91(6H), 5.13(4H), 5.1(2H) |
| 38 | E$_1$–(=)$_2$–I (CH$_3$) | — | C$_{23}$H$_{35}$O$_2$I (470.43) | 1.61(3H), 1.76(3H), 1.8–2.4(6H), 2.16(3H), 3.20(2H), 3.42(2H), 3.68(3H), 3.70(3H), 5.1(2H) |
| 39 | K$_1$–=–I (CH$_3$) | — | C$_{20}$H$_{25}$O$_2$I (424.32) | 1.86(3H), 2.33(3H), 1.8–2.2(4H), 3.36(2H), 3.50(2H), 3.82(6H), 5.1(1H), 7.2–8.2(4H) |
| 40 | K$_1$–(=)$_2$–I (CH$_3$) | — | C$_{25}$H$_{33}$O$_2$I (492.44) | 1.56(3H), 1.83(3H), 2.33(3H), 3.34(2H), 3.50(2H), 3.81(6H), 5.1(2H), 7.2–8.2(4H) |
| 41 | K$_1$–=–≡–I (CH$_3$) | — | C$_{23}$H$_{27}$O$_2$I (462.37) | 1.86(3H), 2.33(3H), 1.8–2.4(4H), 2.44(2H), 3.50(2H), 3.75(2H), 3.81(6H), 7.2–8.2(4H) |
| 42 | Q$_2$–CHO | — | C$_{15}$H$_{22}$O$_5$ (282.34) | 1.78(2H), 2.16(3H), 2.4–2.7(4H), 3.76(3H), 3.79(3H), 3.88(6H), 9.75(1H), b.p.$_{0.7}$ 135–140° C. |
| 43 | Q$_3$–=–CHO (CH$_3$) | — | C$_{20}$H$_{30}$O$_7$ (382.46) | 1.76(3H), 2.14(3H), 2.2–2.6(4H), 3.36(2H), 3.54(3H), 3.56(3H), 3.84(6H), 5.03(4H), 5.08(1H), 9.71(1H) |

TABLE 3-continued

| Ref. Ex. | Product | Starting material (Ref. Ex.) | Formula (M.W.) | NMR [in CDCl$_3$, TMS internal standard, δ(ppm)] |
|---|---|---|---|---|
| 44 | E$_1$~~~CHO | — | C$_{15}$H$_{22}$O$_3$ (250.34) | 1.80(2H), 2.16(6H), 2.21(3H), 2.4–2.7(4H), 3.62(6H), 9.76(1H), b.p.$_1$ 130–140° C. |
| 45 | E$_1$~~~=~~=~~CN | — | C$_{24}$H$_{31}$NO$_2$ (365.52) | 1.4–2.0(6H), 2.1–2.4 (4H), 2.19(6H), 2.24 (3H), 2.4–2.8(4H), 3.13(2H), 3.70(3H), 3.73(3H) |
| 46 | Q$_2$~~~=~~=~~OH | — | C$_{23}$H$_{32}$O$_5$ (388.51) | 1.4–1.8(7H), 2.1–2.4 (6H), 2.17(3H), 2.67 (2H), 3.76(3H), 3.80 (3H), 3.88(6H), 4.20 (2H) |
| 47 | K$_1$~~~=~~=~~OH | — | C$_{25}$H$_{30}$O$_3$ (378.52) | 1.5–1.8(7H), 2.1–2.4 (6H), 2.41(3H), 2.80 (2H), 3.85(3H), 3.89 (3H), 4.20(2H), 7.3–7.5(2H), 7.9–8.1(2H) |
| 48 | Q$_2$~~~=~~=~~OH | 46 | C$_{23}$H$_{36}$O$_5$ (392.54) | 1.2–1.7(7H), 1.9–2.3 (6H), 2.14(3H), 2.55 (2H), 3.76(3H), 3.79 (3H), 3.87(6H), 4.0–4.2(2H), 5.3–5.6(4H) |
| 49 | K$_1$~~~=~~=~~OH | 47 | C$_{25}$H$_{34}$O$_3$ (382.55) | 1.2–1.7(7H), 1.9–2.3 (6H), 2.39(3H), 2.79 (2H), 3.84(3H), 3.87 (3H), 4.0–4.2(2H), 5.3–5.6(4H), 7.3–7.5 (2H), 7.9–8.1(2H) |
| 50 | E$_1$~~~=~~=~~OH | 6 | C$_{23}$H$_{26}$O$_3$ (360.54) | 1.2–1.6(7H), 1.9–2.2 (6H), 2.16(6H), 2.19 (3H), 2.58(2H), 3.62 (3H), 3.64(3H), 4.0–4.2(2H), 5.3–5.6(4H) |

REFERENCE EXAMPLE 51

In toluene (500 ml) was suspended 2,3,5-trimethylphenyl (100 g, 0.735 mole), and to the suspension were added dihydrofuran (56.6 g, 0.735×1.1 mole) and camphorsulfonic acid (0.85 g), followed by stirring at room temperature for 30 minutes. As the reaction proceeded, there occurred dissolution under the evolution of heat. Without isolating and purifying tetrahydrofur-2-yl ether as produced, camphorsulfonic acid (16.1 g) was further added to the reaction solution, followed by stirring at 60° C. for 1.5 hours. After the conclusion of the reaction, the reaction solution was cooled, and saturated sodium hydrogen carbonate (300 ml) was added for neutralization. The organic layer was washed with water, dried (over MgSO$_4$) and freed of the solvent by distillation. The residue was distilled under reduced pressure, thereby yielding 2,3,5-trimethyl-6-(tetrahydrofur-2-yl)phenyl (147 g, 97%, bp$_{1.0}$ 124° to 130° C.).

REFERENCE EXAMPLE 52

In toluene (150 ml) was suspended 2,3-dimethoxy-5-methyl-1,4-benzohydroquinone (18.2 g, 0.1 mole), and to the suspension were added dihydrofuran (15 g, 0.204 mole) and camphorsulfonic acid (0.15 g), followed by stirring at room temperature for 1 hour. Without isolating the product, camphorsulfonic acid (2.2 g) was further added to the reaction solution, followed by stirring at 60° C. for 3 hours. The reaction solution was cooled, washed with water, dried (over MgSO$_4$) and freed of the solvent by distillation. The residue was chromatographed on a column of silica gel, and developing with isopropyl ether yielded 2,3-dimethoxy-5-methyl-6-(tetrahydrofur-2-yl)-1, 4-benzyhydroquinone (20.8 g, 82%, mp. 77° to 78° C.).

REFERENCE EXAMPLES 53 TO 57

By the same procedures as described in Reference Example 51 (Method A) and 52 (Method B), where were obtained the compounds as shown in Table 4.

TABLE 4

| Ref. Ex. | Starting material | Method | Product | Yield | Physical property |
|---|---|---|---|---|---|
| 53 | 2,3,5-trimethylhydroquinone (OH, CH₃, CH₃, CH₃, OH) | B | 2,3,5-trimethyl-6-(tetrahydrofur-2-yl)hydroquinone | 75% | mp. 104–105° C. |
| 54 | 4-tert-butylphenol | A | 2-(tetrahydrofur-2-yl)-4-tert-butylphenol | 57% | oil IR(cm⁻¹): 3500, 1120 |
| 55 | 3,4,5-trimethylphenol | A | 2-(tetrahydrofur-2-yl)-3,4,5-trimethylphenol | 72% | bp$_{1.0}$ 130–135° C. |
| 56 | 2-methyl-1,4-naphthohydroquinone | B | 3-(tetrahydrofur-2-yl)-2-methyl-1,4-naphthohydroquinone | 60% | as the quinone form mp. 46–47° C. |
| 57 | p-cresol | A | 2-(tetrahydrofur-2-yl)-4-methylphenol | 56% | bp$_{0.6}$ 100–106° C. |

REFERENCE EXAMPLE 58

In dimethylformamide (200 ml) was dissolved 2,3,5-trimethyl-6-(tetrahydrofur-2-yl)-1,4-benzohydroquinone (22.2 g, 0.1 mole). The solution was cooled with ice under a nitrogen atmosphere, and 60% sodium hydride (oilborne, 8.8 g, 0.10×2.2 mole) was added, followed by stirring for 15 minutes. Then, methyl iodide (35.5 g, 0.10×2.5 mole) was added dropwise to the mixture over a 15-minute period, followed by stirring for 30 minutes. Ice-cooled water (250 g) was added to the reaction solution, and the product was extracted with isopropyl ether (500 ml). The extract was washed with water, dried and freed of the solvent. The residue was distilled under reduced pressure, thereby yielding 1,4-dimethoxy-2,3,5-trimethyl-6-(tetrahydrofur-2-yl)benzene (24.5 g, 98%, bp$_{1.0}$ 130° to 140° C.).

The dimethoxy compound (24.5 g) obtained in this manner was dissolved in ethyl acetate (250 ml) and, following the addition to the solution of 5% palladium-carbon (2.5 g) and 70% perchloric acid (1 ml), catalytic reduction was conducted at 40° C. After the completion of the reaction, the catalyst was filtered out, and the ethyl acetate solution was washed with aqueous saturated sodium hydrogen carbonate and water, successively. The organic layer was separated, dried and freed of the organic solvent under reduced pressure. Recrystallization of the residue from isopropyl ether-hexane yielded 1,4-dimethoxy-2,3,5-trimethyl-6-(4-hydroxybutyl)benzene (22.2 g, 90%, mp. 88° to 88.5° C.).

REFERENCE EXAMPLE 59

By the same procedure as described in Reference Example 58, 2,3-dimethoxy-5-methyl-6-(tetrahydrofur-2-yl)-1,4-benzohydroquinone (27 g, 0.106 mole) was methylated with methyl iodide, thereby being derived into 1,2,3,4-tetramethoxy-5-methyl-6-(tetrahydrofur-2-yl)benzene (28.5 g, 98%, bp$_{1.0}$ 135° to 138° C.). The catalytic reduction of the compound afforded 1,2,3,4-tetramethoxy-5-methyl-6-(4-hydroxybutyl)benzene (28.2 g, 99%, oily substance).

REFERENCE EXAMPLE 60

In anhydrous methylene chloride (300 ml) were 1,2,3,4-tetramethoxy-5-methyl-6-(4-hydroxybutyl)benzene (28.2 g, 0.1 mole) as obtained in Reference Example 59 and triethylamine (16 g, 0.15 mole), and the solution was cooled to 0° C. A solution of methanesulfonyl chloride (14.3 g, 0.12 mole) in methylene chloride (30 ml) was added dropwise to the solution, followed by stirring for 30 minutes. The reaction solution was washed with water, dilute aqueous phosphoric acid and water, successively, and the organic layer was dried (over MgSO₄) and freed of the solvent. Acetone (300 ml) and sodium iodide (39.0 g, 0.26 mole) were added to the residue, and the mixture was warmed at 50° C. for 2 hours. After the completion of the reaction, acetone was distilled off under reduced pressure, and isopropyl ether (300 ml) and water (200 ml) were added to the residue for extraction of the product. The organic layer was washed with 5% aqueous sodium hydrosulfite and water, successively, and dried (over MgSO₄), followed by distilling off the solvent under reduced pressure. The residue was chromatographed on a column of silica gel, and developing with isopropyl ether-hexane (1:1) yielded 1,2,3,4-tetramethoxy-5-methyl-6-(4-iodobutyl)-benzene (37.0 g, 94%).

REFERENCE EXAMPLE 61

By adding sodium (2.88 g, 0.12 gram atom) and ferric nitrate (50 mg) to liquid ammonia (300 ml), sodium amide was prepared at −60° to −40° C. A solution of 1-tetrahydropyranyloxy-5-hexyne (21.8 g, 0.12 mole) in ether (20 ml) was added to the ammonia solution over a period of 20 minutes, followed by stirring for 40 minutes. A solution of the iodo compound (37.0 g, 0.094 mole) obtained in Reference Example 60 in ether (40 ml) was added dropwise to the mixture over a period of 40 minutes, while maintaining the reaction temperature a −60° to −50° C., followed by stirring at the same temperature for 1 hour and then at −50° to −30° C. for 1 hour. Then, ammonium chloride (50 g) was added to the reaction solution, followed by stirring for 10 minutes. The ammonia was removed, and isopropyl ether (300 ml) and water (300 ml) were added for the extraction of the product. The organic layer was washed with water, dried (over MgSO₄) and freed of the solvent by distillation, thereby yielding the crude product. This was dissolved in methanol (300 ml), and p-toluenesulfonic acid (0.95 g) was added to the solution, followed by stirring at 70° C. for 30 minutes. After the solution was cooled, sodium hydrogen carbonate (2 g) was added, and the methanol was distilled off under reduced pressure. The residue was treated with isopropyl ether (300 ml) and water (200 ml) for the extraction of the product. The organic layer was washed with water, dried (over MgSO₄) and freed of the solvent by distillation under reduced pressure. The residue was chromatographed on silica gel, and developing with isopropyl ether yielded 1,2,3,4-tetramethoxy-5-methyl-6-(10-hydroxydec-5-ynyl)benzene (29.4 g, 86%).

REFERENCE EXAMPLE 62

In ethanol (200 ml) was dissolved the compound (18.2 g, 0.05 mole) obtained in Reference Example 61, and after 5% palladium-carbon (1 g) was added, the catalytic reduction was carried out. At the time when absorption of hydrogen stopped completely, the reaction was completed. The catalyst was filtered out and the ethanol was removed under reduced pressure. The reduced form (18.2 g, 0.05 mole) and 2,6-dicarboxypyridine-1-oxide (27.4 g) were dissolved in acetonitrile (240 ml) and water (120 ml), and after the solution was cooled with ice, a solution of ceric ammonium nitrate (82.2 g, 0.15 mole) in 50% aqueous acetonitrile (360 ml) was added dropwise over a 1-hour period, followed by stirring under ice-cooling for 30 minutes and at room temperature for 30 minutes. After the conclusion of the reaction, insolubles were filtered out, and the acetonitrile was removed under reduced pressure. The product was extracted with isopropyl ether (500 ml), and the extract was washed with saturated aqueous sodium hydrogen carbonate and water, successively, dried (over MgSO₄) and freed of the isopropyl ether. The residue was chromatographed on silica gel, and developing with isopropyl ether yielded 2,3-dimethoxy-5-methyl-6-(10-hydroxydec-5-ynyl)-1,4-benzoquinone (14.5 g, 86%, mp. 52° to 53° C.).

REFERENCE EXAMPLE 63

By subjecting 1,4-dimethoxy-2,3,5-trimethyl-6-(4-hydroxybutyl)benzene obtained in Reference Example 58 to the same reaction as described in Reference Example 60 to 62, there was obtained 2,3,5-trimethyl-6-(10-hydroxydec-5-ynyl)-1,4-benzoquinone (65° to 66° C.).

REFERENCE EXAMPLE 64

In ethyl acetate (50 ml) was dissolved 2,3,5-trimethyl-6-(tetrahydrofur-2-yl)-1,4-benzohydroquinone (2.24 g, 0.01 mole) obtained in Reference Example 53, and after perchloric acid (0.1 ml) and 5% palladium-carbon (500 mg) were added to the solution, the catalytic reduction was carried out at 100 atmospheric pressure. After the completion of the reaction, the catalyst was filtered out, and 5% aqueous solution of ferric chloride (50 ml) was added to the reaction solution, followed by stirring at room temperature for 1 hour. The organic layer was separated, and the water layer was extracted once with ethyl acetate. The extract was combined with the organic layer, followed by washing with water, drying (over MgSO₄) and concentrating. The resulting crude product was chromatographed on silica gel, and developing with isopropyl ether-ethyl acetate (95:5) yielded the desired 2,3,5-trimethyl-6-(4-hydroxybutyl)-1,4-benzoquinone (1.9 g, 88%, mp. 36° to 38° C.).

REFERENCE EXAMPLE 65

By subjecting 2,3-dimethoxy-5-methyl-6-(tetrahydrofur-2-yl)-1,4-benzohydroquinone (2.56 g, 0.01 mole) obtained in Reference Example 52 to the same catalytic reduction and oxidation reaction as described in Reference Example 64, there was obtained the desired 2,3-dimethoxy-5-methyl-6-(4-hydroxybutyl)-1,4-benzoquinone (2.17 g, 84%, oily substance).

IR absorptoin spectrum $\nu_{max}^{film}(cm^{-1})$: 3400(OH), 1660, 1640, 1610(quinone).

EXAMPLES OF PHARMACEUTICAL COMPOSITION

| (A) Capsule | |
|---|---|
| (1) Compound of Example 17 | 50 mg |
| (2) Cellulose fine powder | 30 mg |
| (3) Lactose | 37 mg |
| (4) Magnesium stearate | 3 mg |
| Total | 120 mg |

All the materials were mixed and filled into a gelatin capsule.

| (B) Soft Capsule | |
|---|---|
| (1) Compound of Example 31 | 50 mg |
| (2) Corn starch oil | 100 mg |
| Total | 150 mg |

A mixed solution of (1) and (2) were prepared and filled into a soft capsule by a conventional manner.

| (C) Tablet | |
|---|---|
| (1) Compound of Example 32 | 50 mg |
| (2) Lactose | 34 mg |
| (3) Corn starch | 10.6 mg |
| (4) Corn starch (gelatinized) | 5 mg |
| (5) Magnesium stearate | 0.4 mg |
| (6) Calcium carboxymethyl cellulose | 20 mg |
| Total | 120 mg |

All the materials were mixed and compressed by a tabletting machine to prepare a tablet in accordance with a conventional manner.

What is claimed is:

1. A compound of the formula:

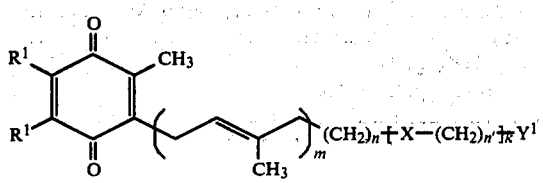

wherein $R^1$ is methyl or methoxy, or the two $R^1$ groups jointly represent —CH=CH—CH=CH—,
X is —CH=CH— or —C≡C—,
$Y^1$ is hydroxyl,
m is zero or an integer of 1 to 3,
n is zero or an integer of 1 to 10,
n' is an integer of 1 to 5,
k is an integer of 1 to 3, and
when k is 2 or 3, n' is optionally variable within the range of 1 to 5 in each occurrence of the —X—$(CH_2)_{n'}$— group,
or its hydroquinone form,
or a pharmaceutically acceptable salt thereof.

2. The compound according to claim 1, which is 2,3-dimethoxy-5-methyl-6-(9-hydroxynon-5-ynyl)-1,4-benzoquinone.

3. The compound according to claim 1, which is 2,3,5-trimethyl-6-(12-hydroxy-5,10-dodecadiynyl)-1,4-benzoquinone.

4. The compound according to claim 1, which is 2,3-dimethoxy-5-methyl-6-(12-hydroxy-5,10-dodecadiynyl)-1,4-benzoquinone.

5. The compound according to claim 1, which is 2,3-dimethoxy-5-methyl-6-[12-hydroxy-(Z,Z)-5,10-dodecadienyl]-1,4-benzoquinone.

6. The compound according to claim 1, which is 2,3,5-trimethyl-6-[12-hydroxy-(Z,Z)-5,10-dodecadienyl]-1,4-benzoquinone.

7. A compound of the formula:

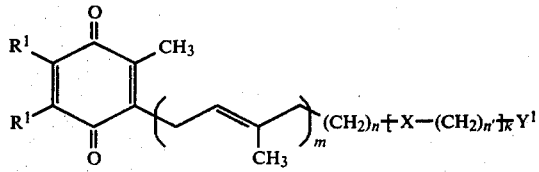

wherein $R^1$ is methyl or methoxy, or the two $R^1$ groups jointly represent —CH=CH—CH=CH—,
X is —CH=CH— or —C≡C—,
$Y^1$ is hydrogen, carboxyl, cyano, $C_{2-4}$ alkanoyloxy, benzoyloxy or —COZ in which Z is amino or mono- or di-$C_{1-4}$ alkylamino,
m is zero or an integer of 1 to 3,
n is zero or an integer of 1 to 10,
n' is an integer of 1 to 5,
k is an integer of 1 to 3, and
when k is 2 or 3, n' is optionally variable within the range of 1 to 5 in each occurrence of the —X—$(CH_2)_{n'}$— group,
with the proviso that there are 8–15 carbon atoms in series between the quinone ring and $Y^1$,
or its hydroquinone form,
or a pharmaceutically acceptable salt thereof.

8. A compound according to claim 7, which is in the quinone form.

9. A compound according to claim 7, wherein $R^1$ is methyl or methoxy, X is —C≡C—, and m is zero.

10. A compound according to claim 7, wherein $Y^1$ is carboxyl, cyano or —COZ in which Z is amino or $C_{1-4}$ alkylamino.

11. A compound according to claim 7, wherein m is zero or 1, n is an integer of 1 to 4, n' is an integer of 1 to 3 and k is 1 or 2.

12. A pharmaceutical composition suitable for suppressing the production of SRS-A in a mammal which comprises, as an active ingredient, an effective amount of a compound of the formula:

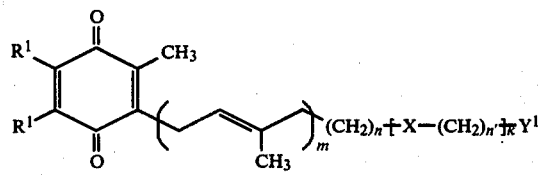

wherein $R^1$ is methyl or methoxy, or the two $R^1$ groups jointly represent —CH=CH—CH=CH—,
X is —CH=CH— or —C≡C—,
$Y^1$ is hydroxyl,
m is zero or an integer of 1 to 3,
n is zero or an integer of 1 to 10,
n' is an integer of 1 to 5,
k is an integer of 1 to 3, and
when k is 2 or 3, n' is optionally variable within the range of 1 to 5 in each occurrence of the —X—$(CH_2)_{n'}$— group,
or its hydroquinone form,
or a pharmaceutically acceptable salt thereof,
and a pharmaceutically acceptable carrier or excipient therefor.

13. A pharmaceutical composition suitable for suppressing the production of SRS-A in a mammal which comprises, as an active ingredient, an effective amount of a compound of the formula:

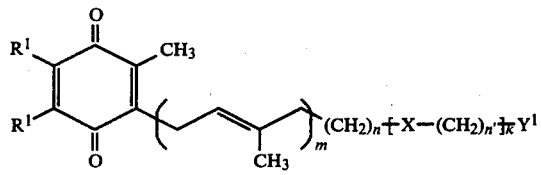

wherein $R^1$ is methyl or methoxy, or the two $R^1$ groups jointly represent —CH=CH—CH=CH—,
X is —CH=CH— or —C≡C—, $Y^1$ is hydrogen, carboxyl, cyano, $C_{2-4}$ alkanoyloxy, benzoyloxy or —COZ in which Z is amino or mono- or di-$C_{1-4}$ alkylamino, m is zero or an integer of 1 to 3, n is zero or an integer of 1 to 10, n' is an integer of 1 to 5, k is an integer of 1 to 3, and when k is 2 or 3, n' is optionally variable within the range of 1 to 5 in each occurrence of the —X—$(CH_2)_{n'}$— group, with the proviso that there are 8–15 carbon atoms in series between the quinone ring and $Y^1$, or its hydroquinone form, or a pharmaceutically acceptable salt thereof, and a pharmaceutically acceptable carrier or excipient therefor.

14. A method for suppressing the production of SRS-A in a mammal in need thereof, which comprises administering to said mammal an effective amount of a compound of the formula:

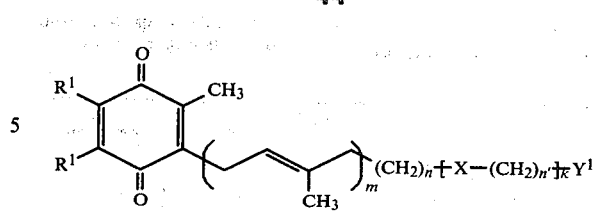

wherein $R^1$ is methyl or methoxy, or the two $R^1$ groups jointly represent —CH=CH—CH=CH—, X is —CH=CH— or —C≡C—, $Y^1$ is hydrogen, hydroxyl, carboxyl, cyano, $C_{2-4}$ alkanoyloxy, benzoyloxy or —COZ in which Z is amino or mono- or di-$C_{1-4}$ alkylamino, m is zero or an integer of 1 to 3, n is zero or an integer of 1 to 10, n' is an integer of 1 to 5, k is an integer of 1 to 3, and when k is 2 or 3, n' is optionally variable within the range of 1 to 5 in each occurrence of the —X—$(CH_2)_{n'}$— group, or its hydroquinone form, or a pharmaceutically acceptable salt thereof.

* * * * *

REEXAMINATION CERTIFICATE (1090th)
United States Patent [19]
Terao et al.

[11] B1 4,393,075
[45] Certificate Issued  Jul. 4, 1989

[54] QUINONE COMPOUNDS AND THEIR USE IN SUPPRESSING THE PRODUCTION OF SRS-A IN MAMMALS

[75] Inventors: Shinji Terao, Toyonaka; Mitsuru Shiraishi, Suita; Yoshitaka Maki, Kyoto, all of Japan

[73] Assignee: Takeda Chemical Industries, Ltd.

Reexamination Request:
No. 90/001,640, Nov. 18, 1988

Reexamination Certificate for:
Patent No.: 4,393,075
Issued: Jul. 12, 1983
Appl. No.: 248,042
Filed: Mar. 26, 1981

[30] Foreign Application Priority Data
Apr. 14, 1980 [JP] Japan ............... 55-49433
Apr. 30, 1980 [JP] Japan ............... 55-58464
Dec. 27, 1980 [JP] Japan ............... 55-186622

[51] Int. Cl.$^4$ ............... A61K 31/12; A61K 31/275; C07C 50/00
[52] U.S. Cl. ............... 514/519; 260/396 R; 514/520; 514/532; 514/546; 514/557; 514/559; 514/568; 514/569; 514/621; 514/622; 514/675; 514/678; 514/679; 514/682; 514/826; 558/410; 560/106; 560/107; 560/231; 560/255; 562/466; 562/508; 564/123; 564/180; 568/811; 568/823
[58] Field of Search ............... 260/396 R; 514/520, 514/690, 679, 682, 519

[56] References Cited
U.S. PATENT DOCUMENTS
3,974,187  8/1976  Wan et al. ............... 260/396 R FOREIGN PATENT DOCUMENTS
52-87130  7/1977  Japan .
896719  5/1962  United Kingdom .
1147612  4/1969  United Kingdom .
1449043  9/1976  United Kingdom .
1512541  6/1978  United Kingdom .

OTHER PUBLICATIONS
Wantanabe et al., Chem. Pharm. Bull., 26(3) 774-783 (1978).

Primary Examiner—Leonard Schenkman

[57] ABSTRACT

New quinone compounds of the formula:

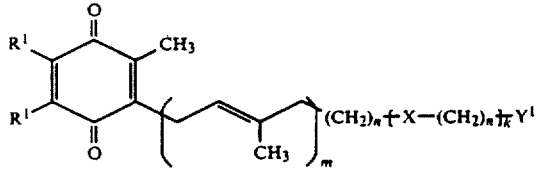

wherein $R^1$ is methyl or methoxy, or the two $R^1$ groups jointly represent —CH=CH—CH=CH—; X is —CH=CH— or —C≡C—; $Y^1$ is hydrogen, hydroxyl, carboxyl, cyano, acyloxy or —COZ in which Z is amino which may be substituted; m is zero or an integer of 1 to 3; n is zero or an integer of 1 to 10; n' is an integer of 1 to 5; k is an integer of 1 to 3; and when k is 2 or 3, n' is optionally variable within the range of 1 to 5 in each occurrence of the —X—(CH$_2$)$_{n'}$ group; and their hydroquinone forms and salts, have useful physiological activities such as antiasthmatic, antiallergic and blood-pressure decreasing activities.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–6 and 12–14 is confirmed.

Claim 7 is determined to be patentable as amended.

Claims 8–11, dependent on an amended claim, are determined to be patentable.

7. A compound of the formula:

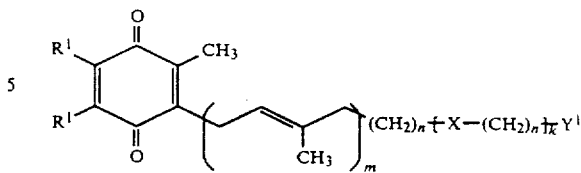

wherein $R^1$ is methyl or methoxy, or the two $R^1$ groups jointly represent —CH=CH—CH=CH—,
X is —CH=CH— or —C≡C—,
$Y^1$ is [hydrogen,] carboxyl, cyano, $C_{2-4}$ alkanoyloxy, benzoyloxy or —COZ in which Z is amino or mono- or di-$C_{1-4}$ alkylamino,
m is zero or an integer of 1 to 3,
n is zero or an integer of 1 to 10,
n' is an integer of 1 to 5,
k is an integer of 1 to 3, and
when k is 2 or 3, n' is optionally variable within the range of 1 to 5 in each occurrence of the —X—$(CH_2)_{n'}$ group,
with the proviso that there are 8–15 carbon atoms in series between the quinone ring and $Y^1$,
or its hydroquinone form,
or a pharmaceutically acceptable salt thereof.

* * * * *